United States Patent
Yamashita

(10) Patent No.: US 10,047,378 B2
(45) Date of Patent: Aug. 14, 2018

(54) METHOD FOR RECOVERING SELENIUM

(75) Inventor: Mitsuo Yamashita, Tokyo (JP)

(73) Assignee: SHIBAURA INSTITUTE OF TECHNOLOGY, Tokyo (JP)

(*) Notice: Subject to any disclaimer, the term of this patent is extended or adjusted under 35 U.S.C. 154(b) by 693 days.

(21) Appl. No.: 14/241,693

(22) PCT Filed: Feb. 9, 2012

(86) PCT No.: PCT/JP2012/052922
§ 371 (c)(1),
(2), (4) Date: Jun. 25, 2014

(87) PCT Pub. No.: WO2013/031252
PCT Pub. Date: Mar. 7, 2013

(65) Prior Publication Data
US 2014/0302578 A1    Oct. 9, 2014

(30) Foreign Application Priority Data

Sep. 2, 2011 (JP) ................. 2011-191309

(51) Int. Cl.
*C12P 3/00* (2006.01)
*C02F 3/34* (2006.01)
*C12R 1/38* (2006.01)
*C02F 3/00* (2006.01)
*C02F 101/10* (2006.01)

(52) U.S. Cl.
CPC ............. *C12P 3/00* (2013.01); *C02F 3/006* (2013.01); *C02F 3/34* (2013.01); *C12R 1/38* (2013.01); *C02F 2101/106* (2013.01); *C02F 2209/001* (2013.01); *C02F 2209/02* (2013.01); *C02F 2209/06* (2013.01); *C02F 2209/22* (2013.01); *C02F 2209/44* (2013.01); *Y02W 10/37* (2015.05)

(58) Field of Classification Search
CPC ............. C12P 3/00; C02F 3/34; C12R 1/38
See application file for complete search history.

(56) References Cited

U.S. PATENT DOCUMENTS

| 4,605,544 A * | 8/1986 | Bjornberg ............. C01B 19/008 423/508 |
| 6,183,644 B1 | 2/2001 | Adams et al. |

FOREIGN PATENT DOCUMENTS

| EP | 0112310 A1 | 6/1984 |
| JP | 10-084948 | 4/1998 |
| JP | 2010-142166 | 7/2010 |
| JP | 2011-063882 | 3/2011 |

OTHER PUBLICATIONS

McDonald et al., Producer responsibility and recyling solar photovoltaic modules, Energy Policy, vol. 38, 2010, p. 7041-7047.*
Winkel et al., Quantitative and Qualitative trapping of volatile methylated selenium species entrained through nitric acid., Environmental Science & Technology, vol. 44, p. 382-387, 2010.*
Kuroda et al., "Characterization of Pseudomonas stutzeri NT-1 capable of removing soluble selenium from the aqueous phase under aerobic conditions", Journal of Bioscience and Bioengineering, Jun. 14, 2011, pp. 259-264, 112 (3).
Notaguchi et al., "Koki Jokenka ni Okeru Pseudomonas stutzeri NT-1 no Selenium Kangen Tokusei", Japanese Journal of Water Treatment Biology, 2008, pp. 15 (No. 28).
Lortie et al., "Reduction of Selenate and Selenite to Elemental Selenium by a Pseudomonas stutzeri Isolate", Appl Environ Microbiol., 1992, pp. 4042-4044, 58 (12).
The International Preliminary report on patentability issued with respect to International Application No. PCT/JP2012/052992, dated Mar. 6, 2014.
Search report issued with respect to International application No. PCT/JP2012/052922, dated Apr. 3, 2012.
Garbisu et al., "Bacterial reduction of selenite to elemental selenium", Chemical Geology 132 (1996), pp. 199-204.
European search report issued with respect to application No. 12827435.4, dated Mar. 18, 2015.
Office Action dated Apr. 6, 2017 issued in corresponding European Patent Office Patent Application No. 12827435.4. In English.

* cited by examiner

*Primary Examiner* — Taeyoon Kim
*Assistant Examiner* — Tiffany Maureen Gough
(74) *Attorney, Agent, or Firm* — Greenblum & Bernstein, P.L.C.

(57) ABSTRACT

An object of the present invention is to provide a method for efficiently recovering solid selenium or gaseous selenium from wastewater/waste using a microorganism. The present invention provides a method for recovering selenium, comprising reducing a water-soluble selenium compound so as to produce elemental selenium or gaseous selenium by allowing a sample containing a water-soluble selenium compound to come into contact at a temperature which is more than 35° C. and is 40° C. or less at pH 7.0 to 9.4 with a microorganism capable of producing elemental selenium or gaseous selenium through reduction of a water-soluble selenium compound.

14 Claims, 22 Drawing Sheets

[Fig. 1]
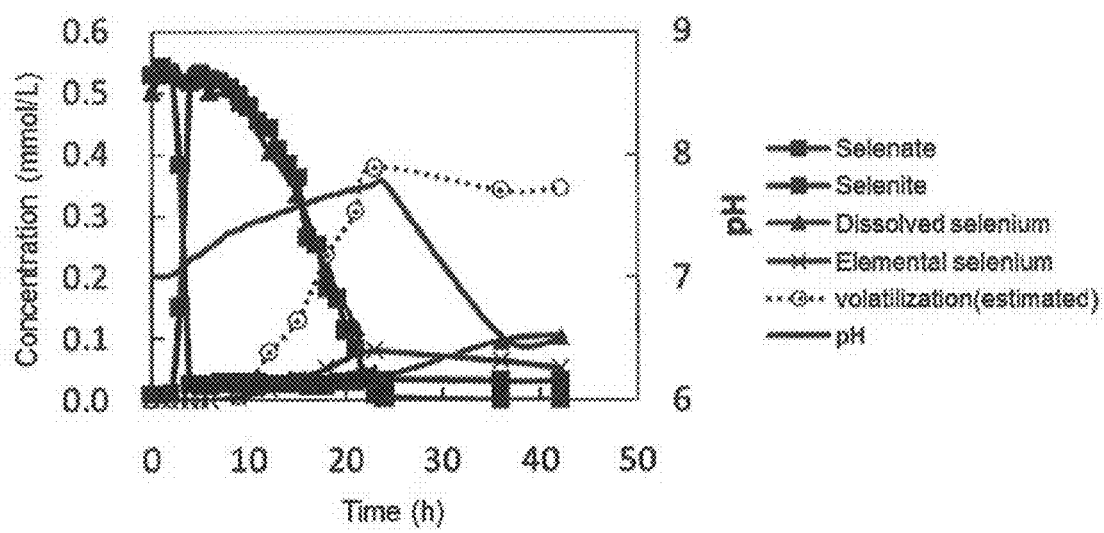
[Fig. 2]
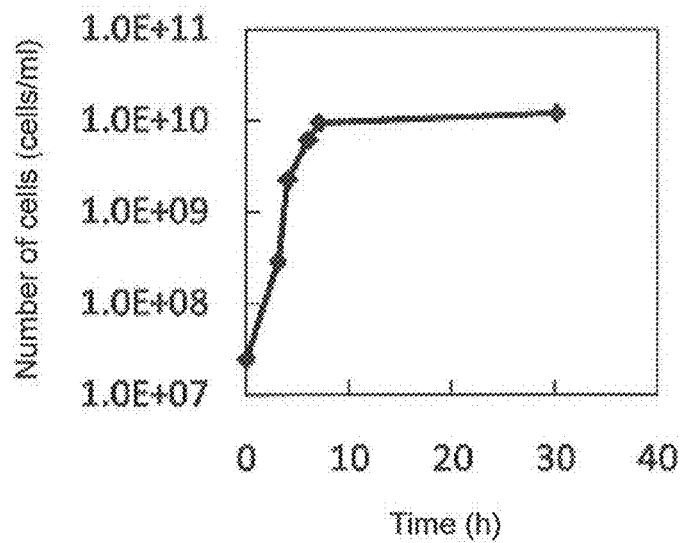

[Fig. 3]
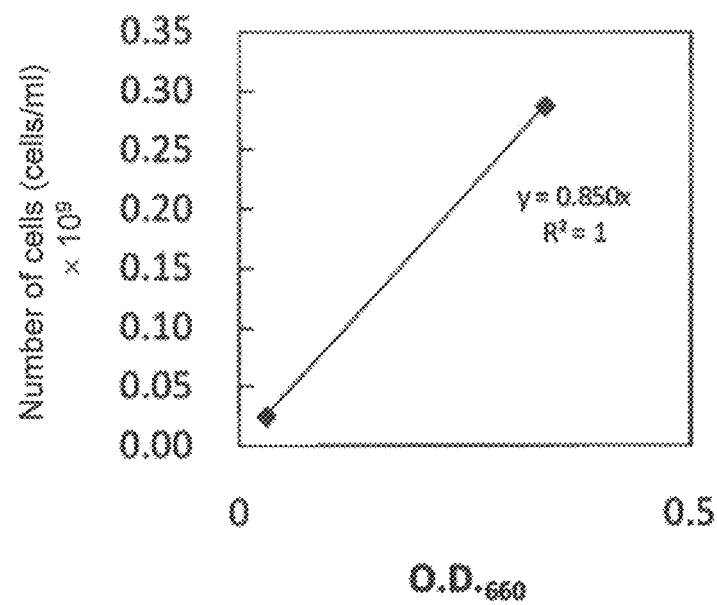
[Fig. 4]
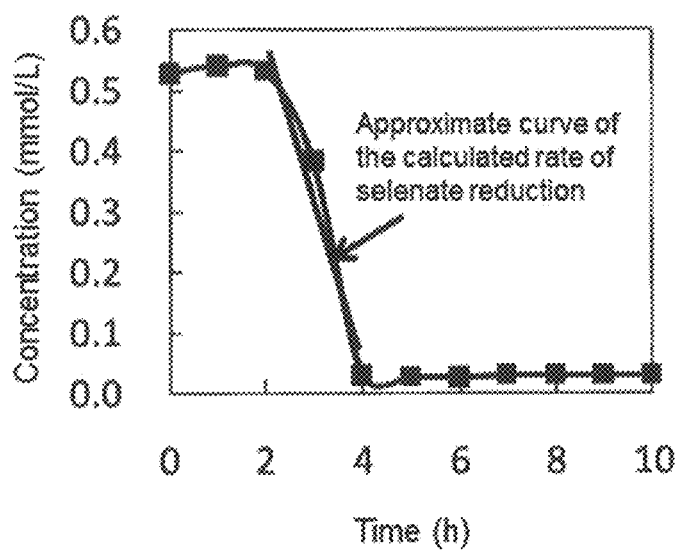

[Fig. 5]
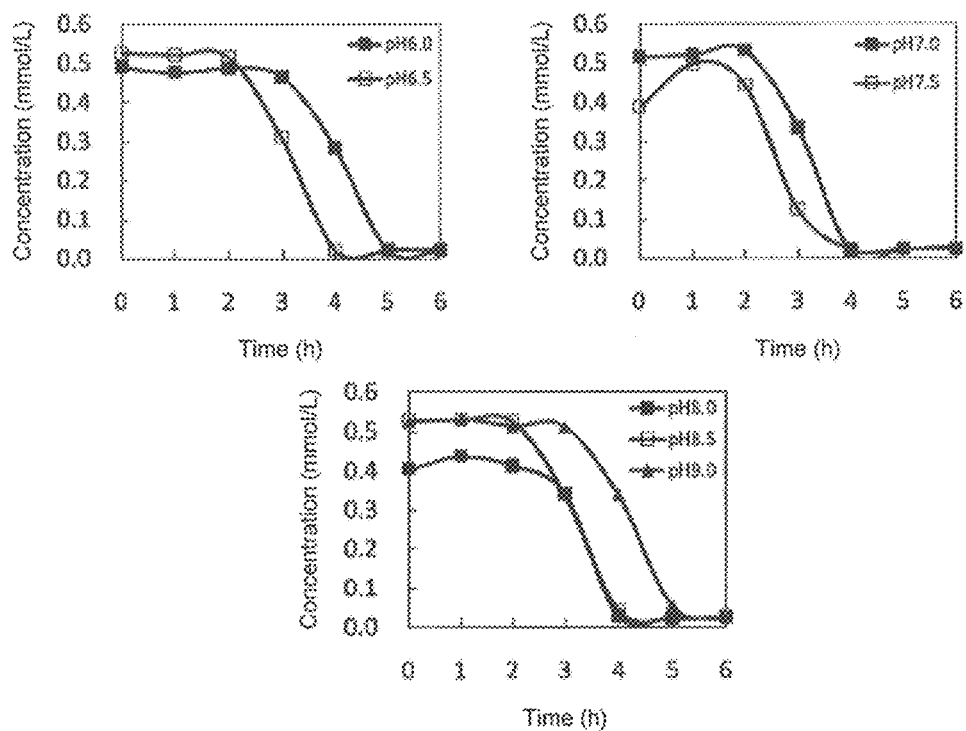
[Fig. 6]
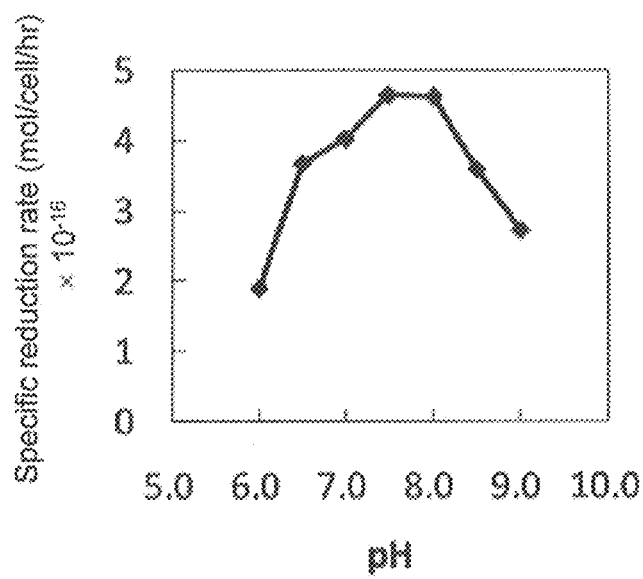

[Fig. 7]
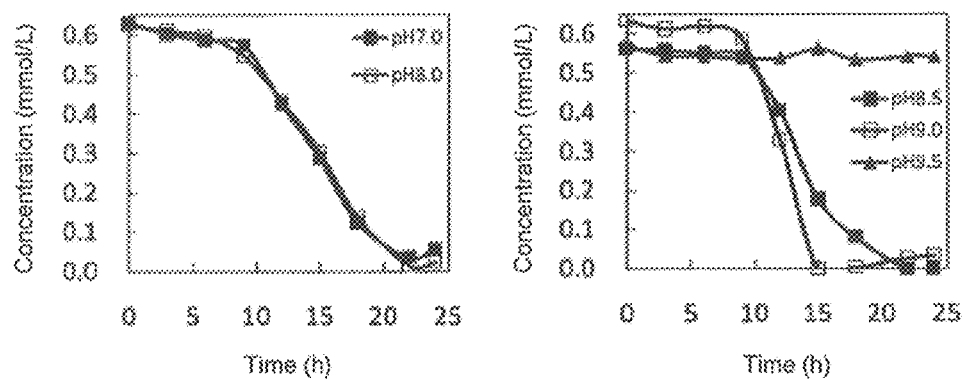
[Fig. 8]
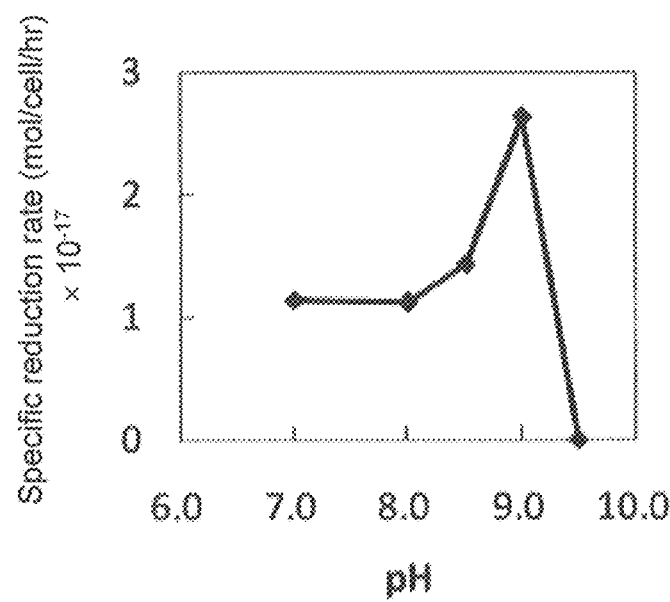

[Fig. 9]
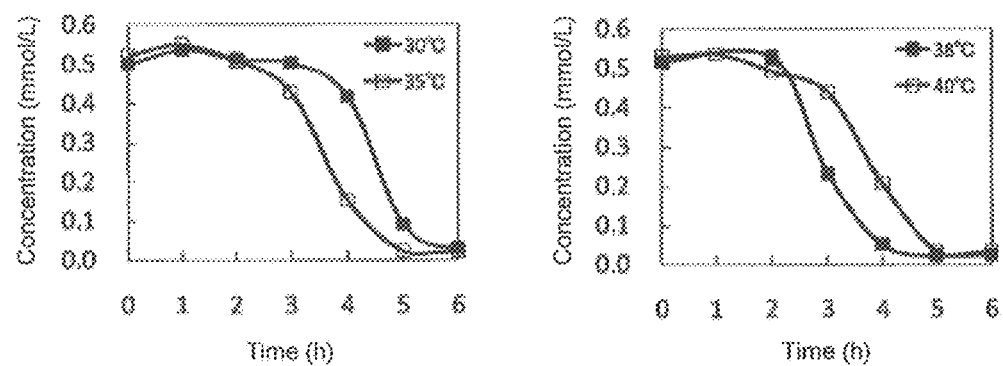
[Fig. 10]
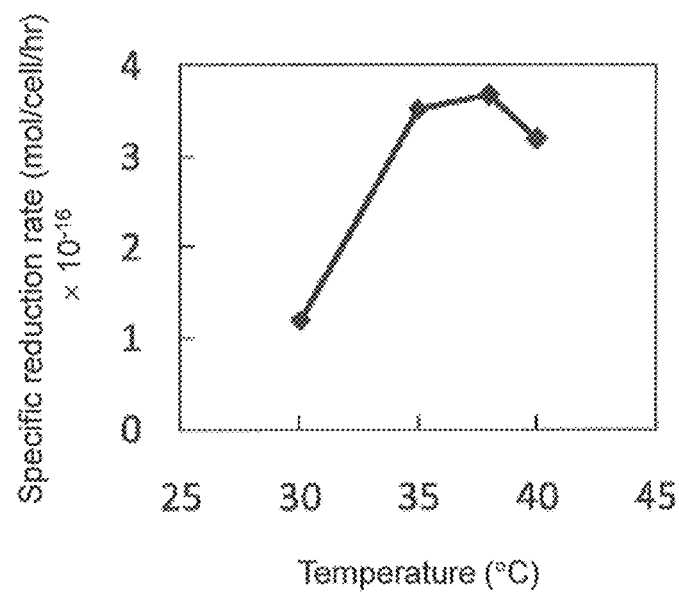

[Fig. 11]
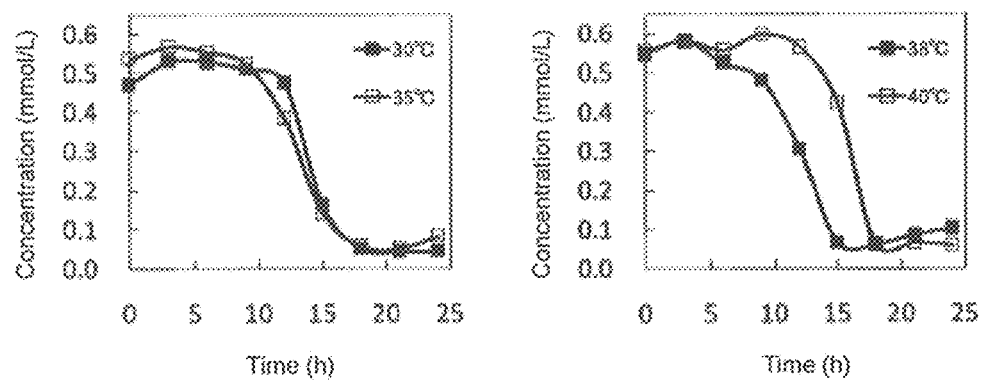
[Fig. 12]
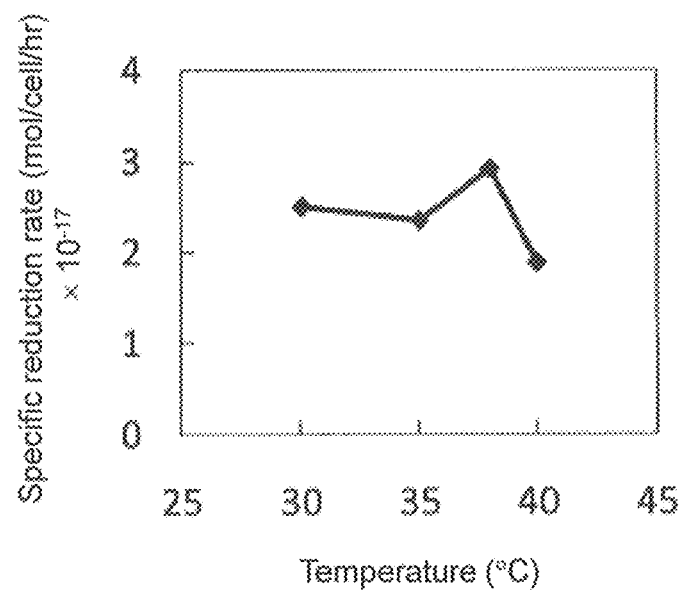

[Fig. 13]
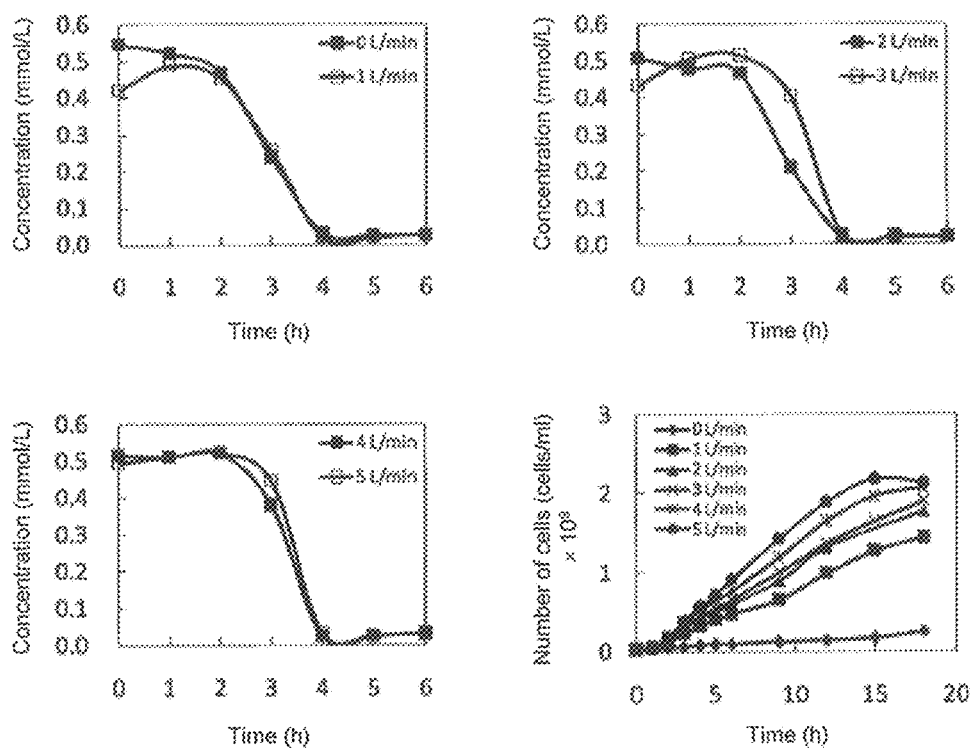
[Fig. 14]
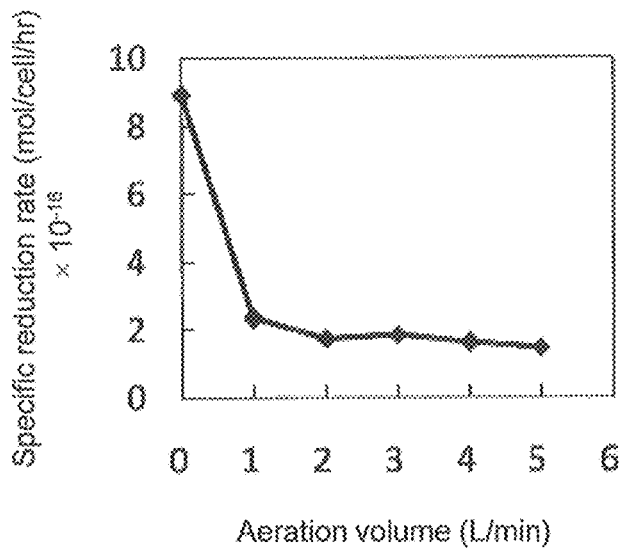

[Fig. 15]
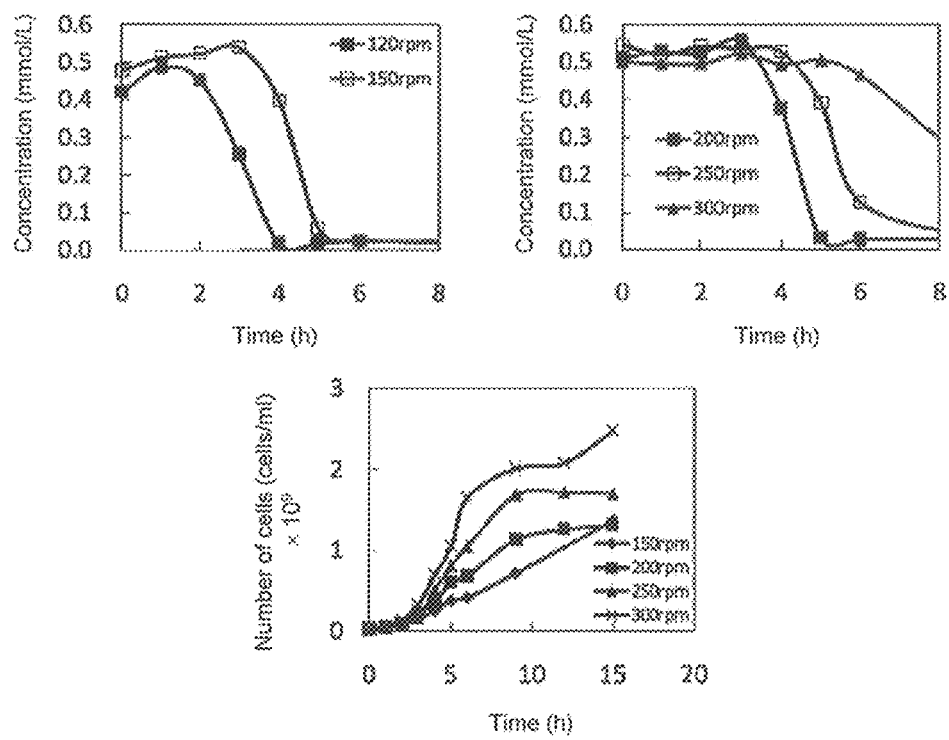
[Fig. 16]
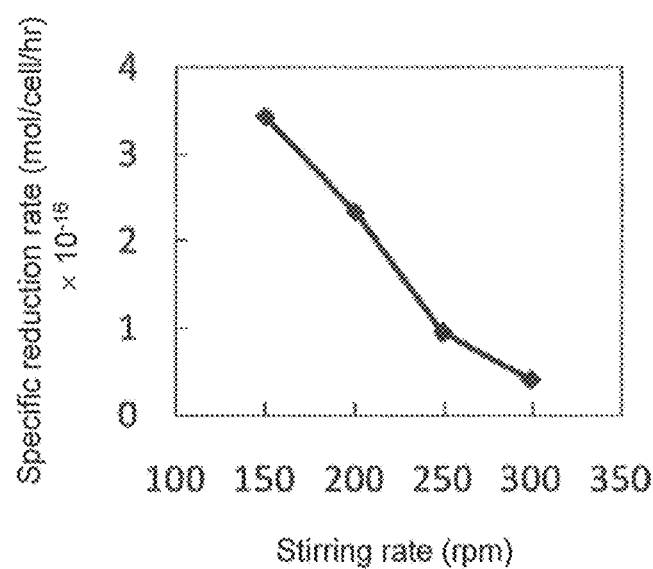

[Fig. 17]
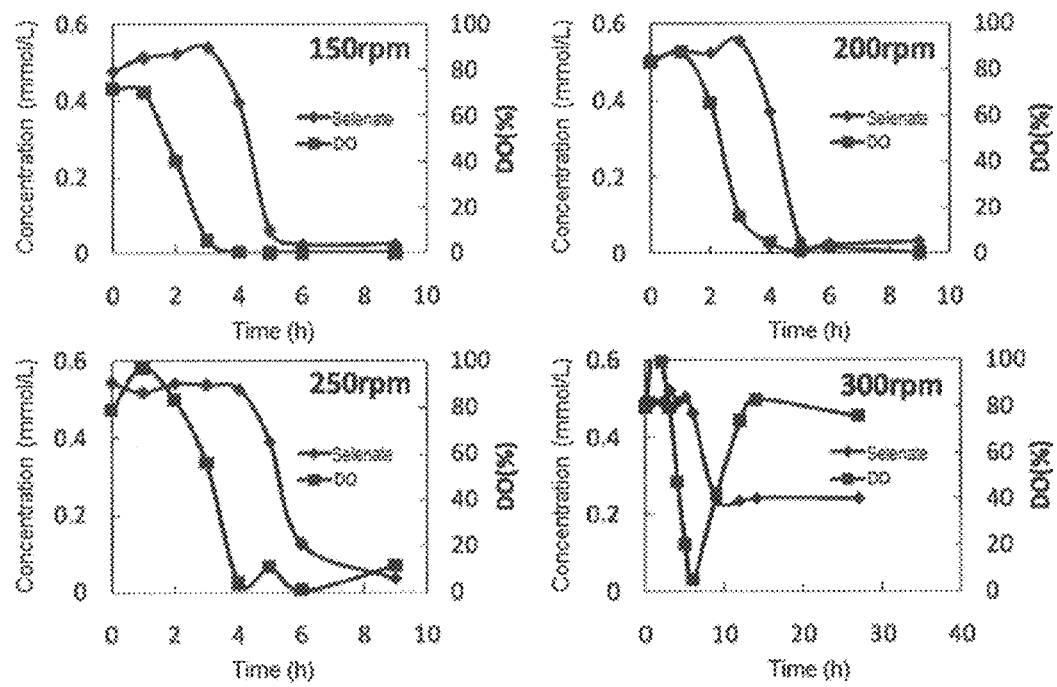
[Fig. 18]
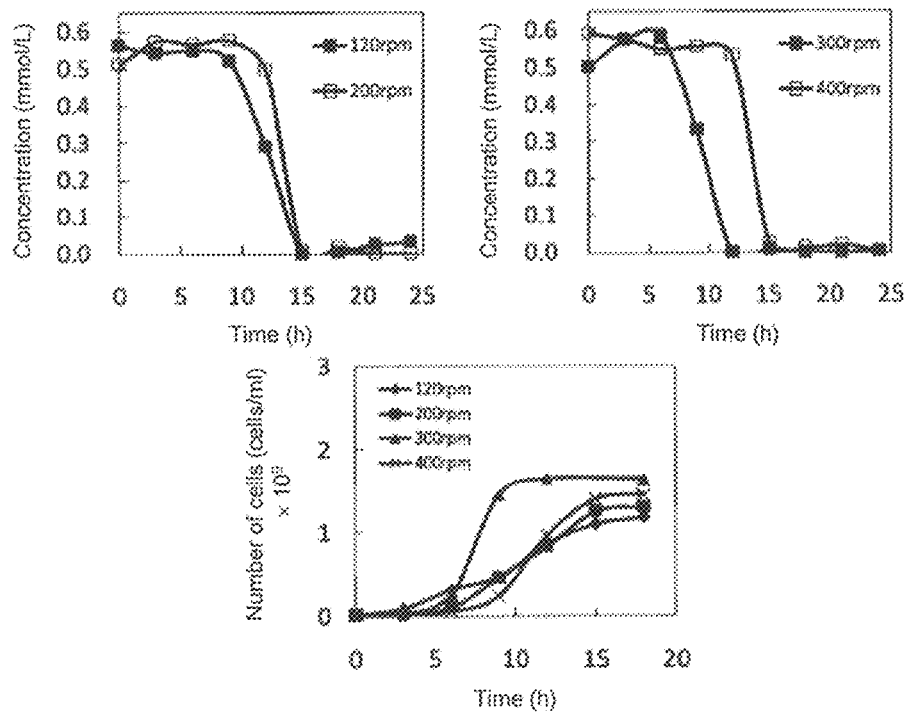

[Fig. 19]
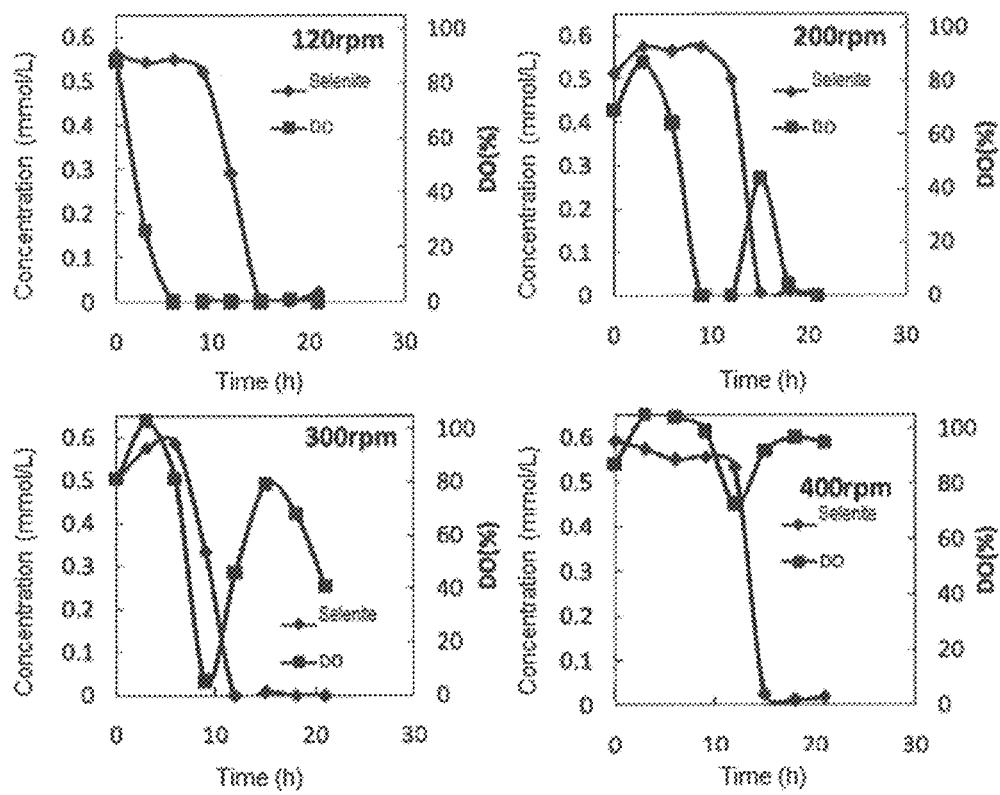
[Fig. 20]
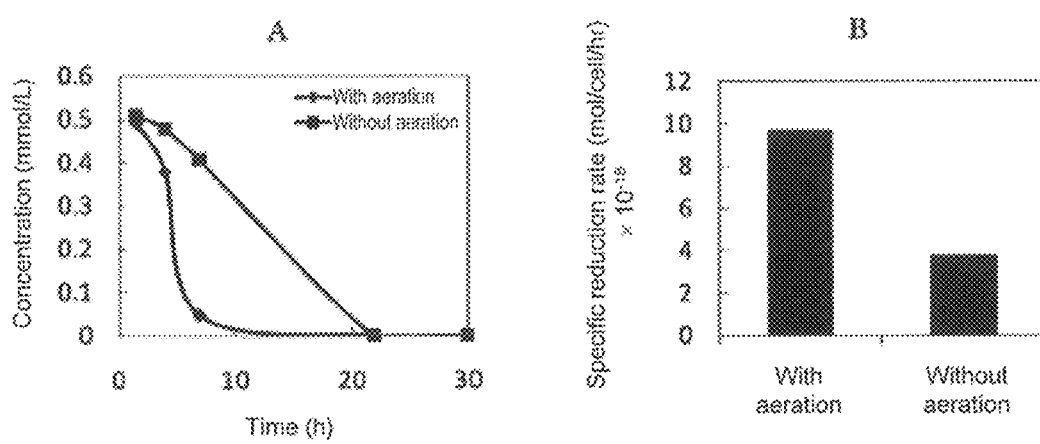

[Fig. 21]
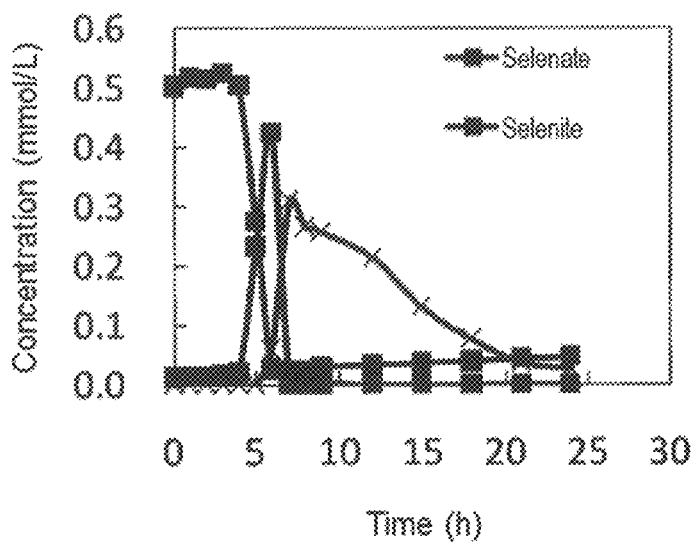
[Fig. 22]
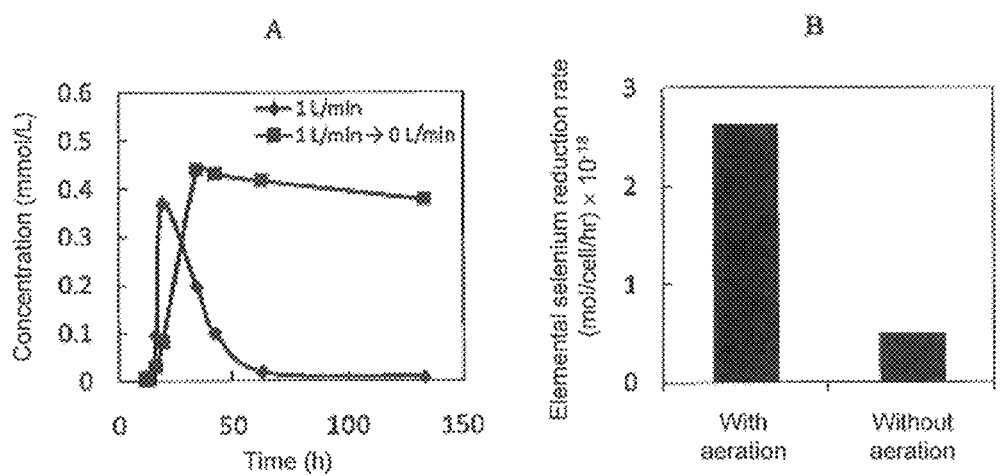

[Fig. 23]
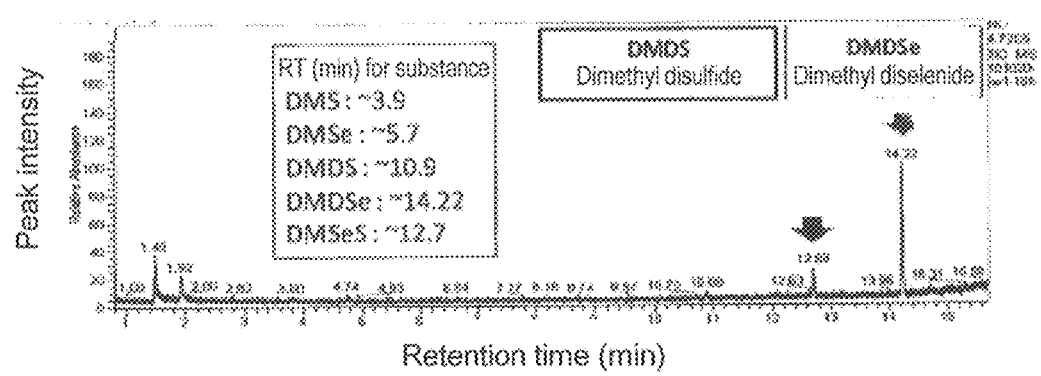
[Fig. 24]
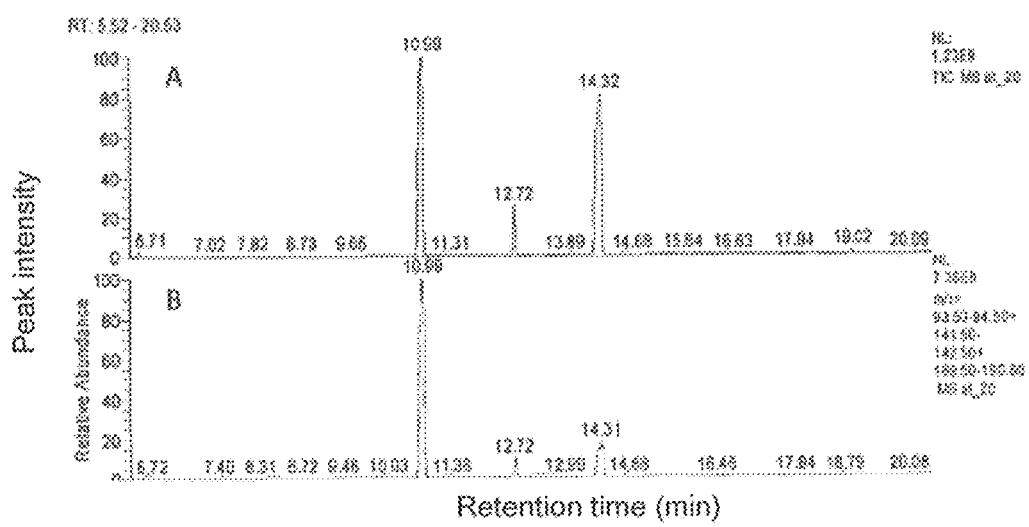

[Fig. 25]
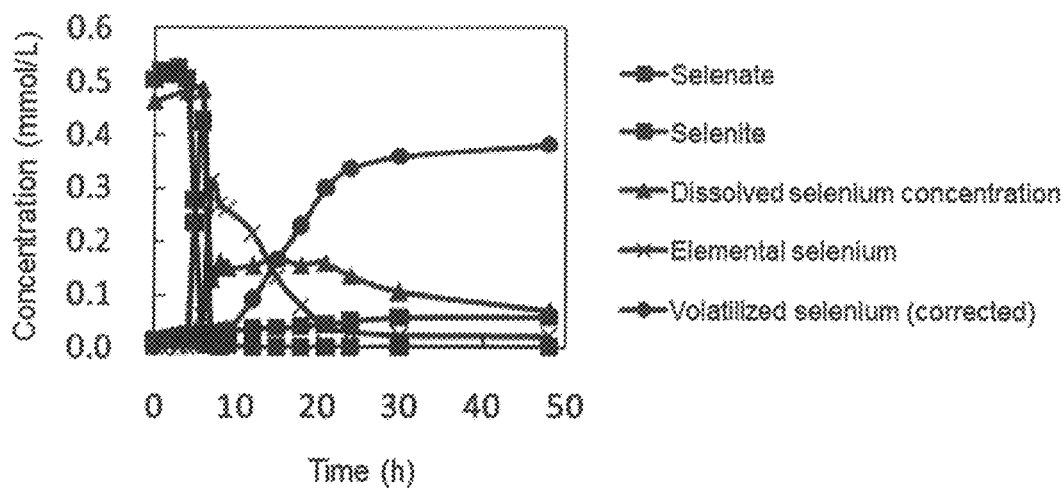
[Fig. 26]
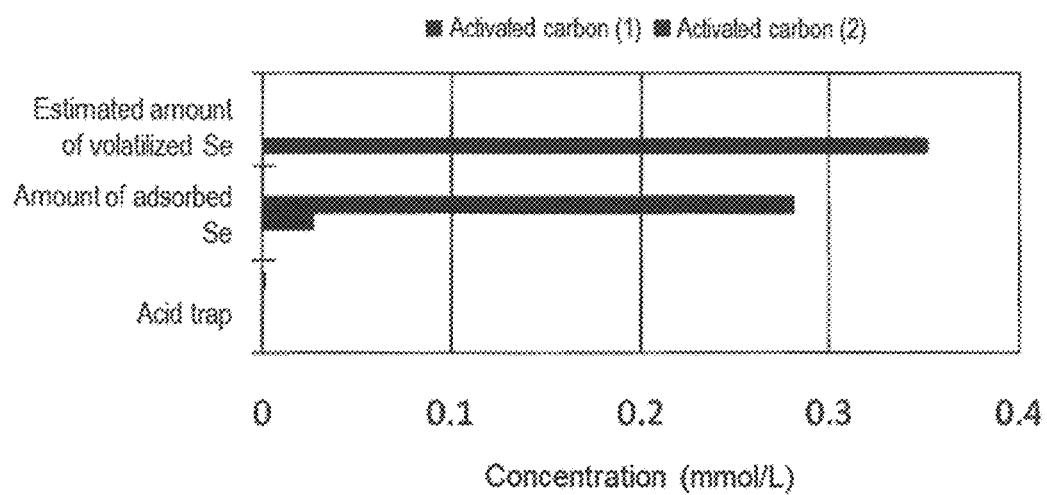

[Fig. 27]
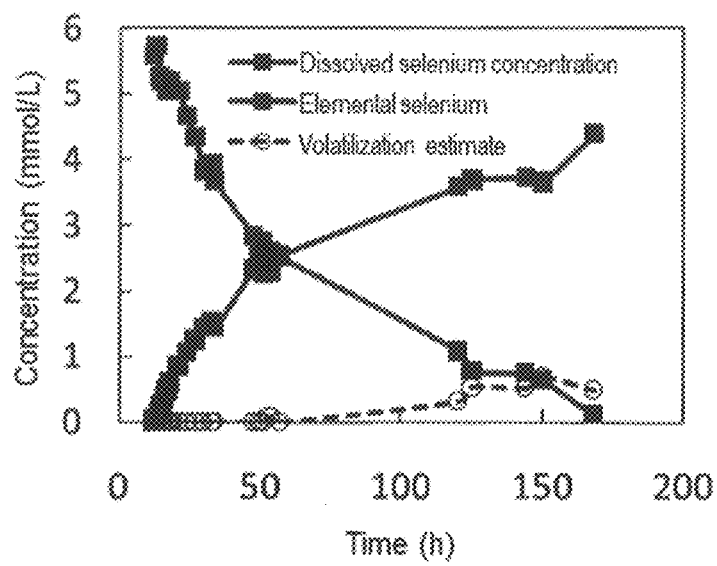
[Fig. 28]
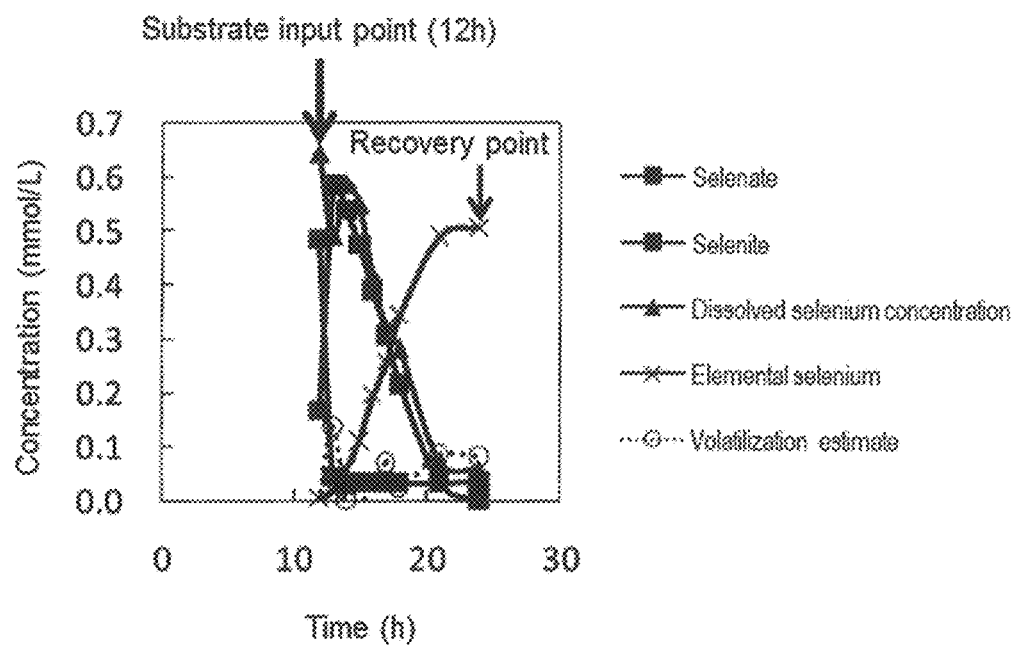

[Fig. 29]
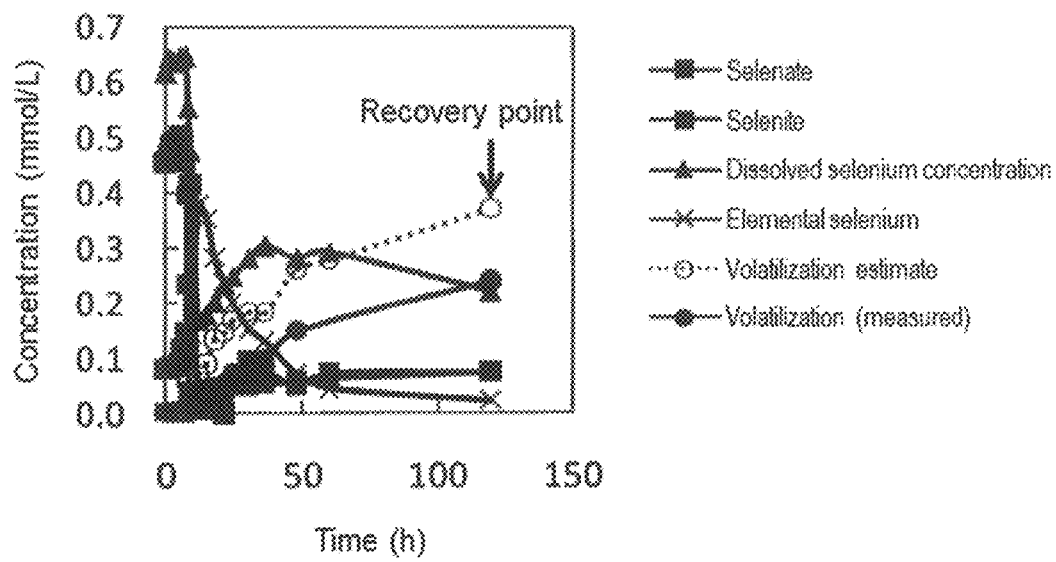
[Fig. 30]
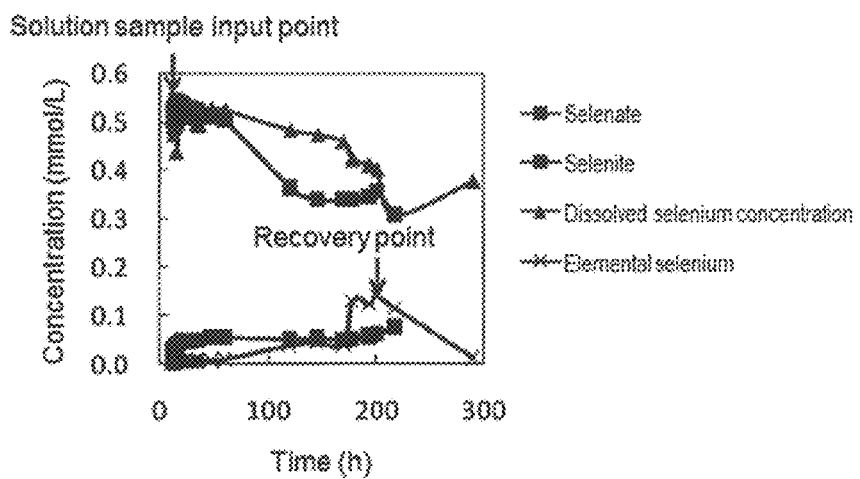

[Fig. 31]
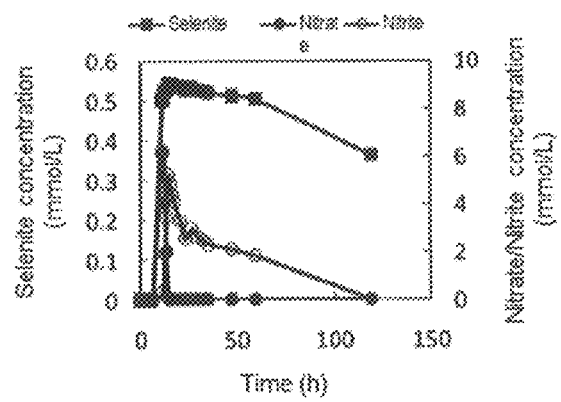
[Fig. 32]
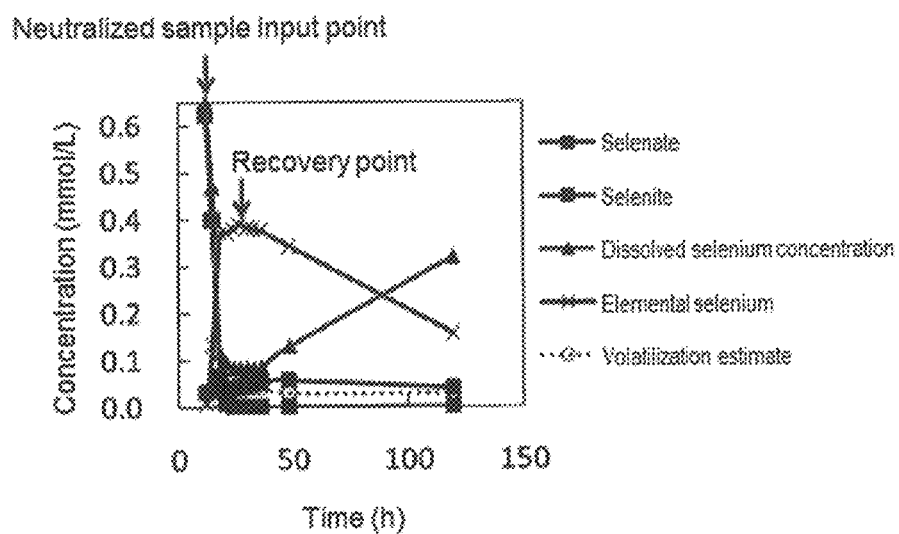

[Fig. 33]
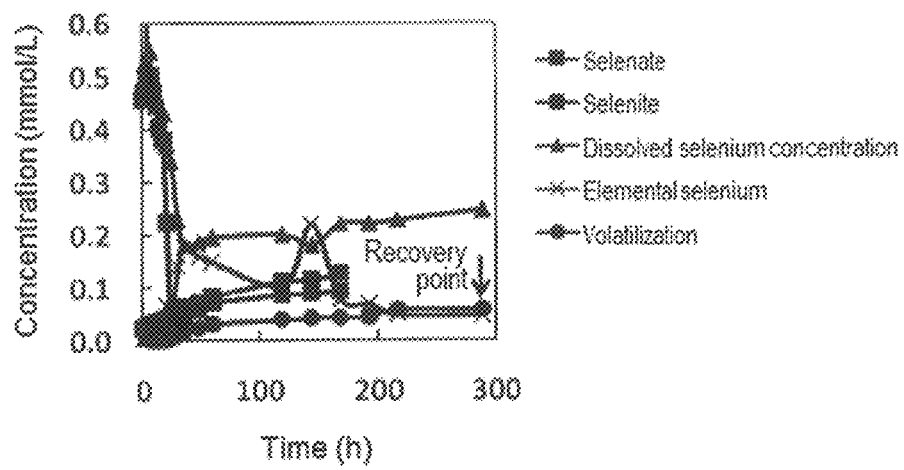
[Fig. 34]
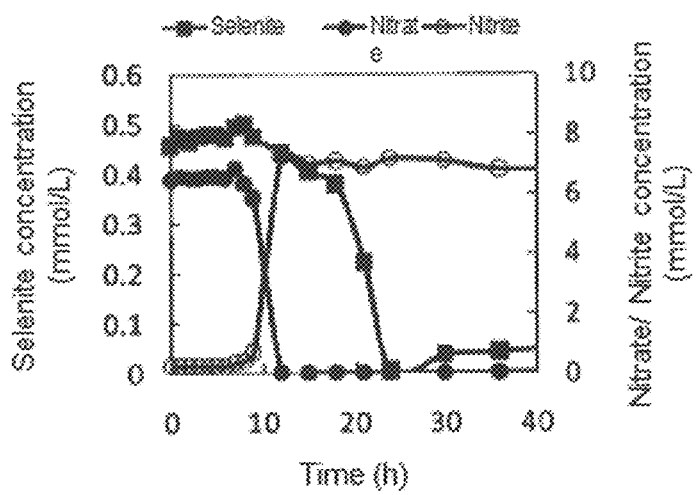

[Fig. 35]
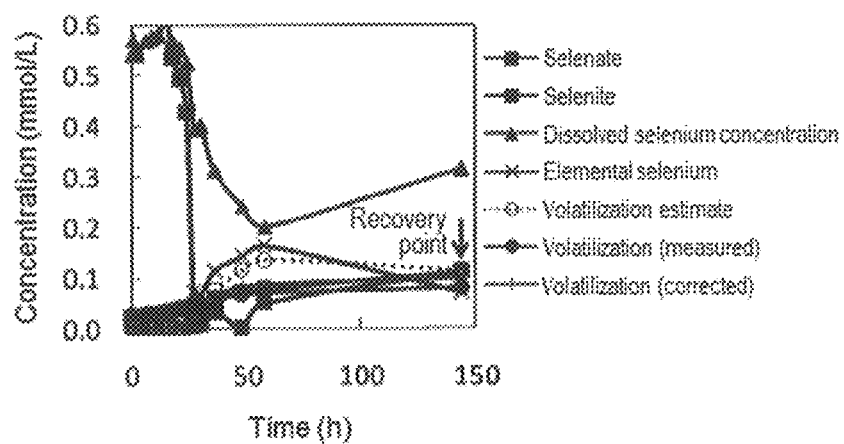
[Fig. 36]
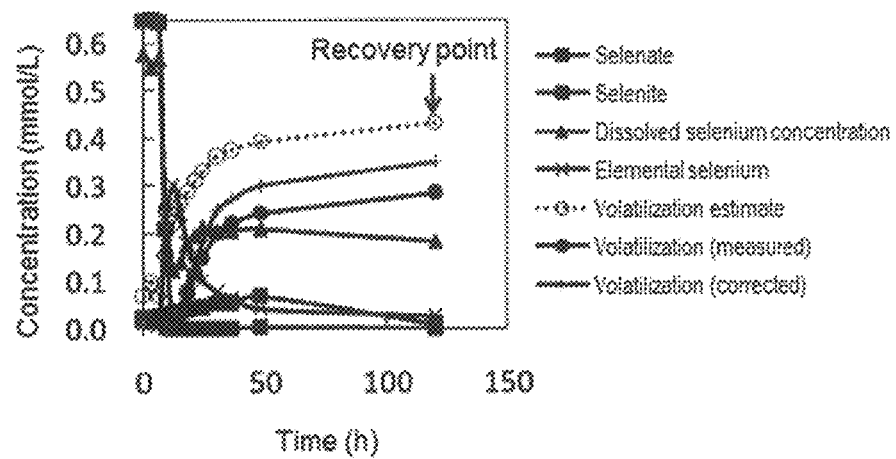

[Fig. 37]
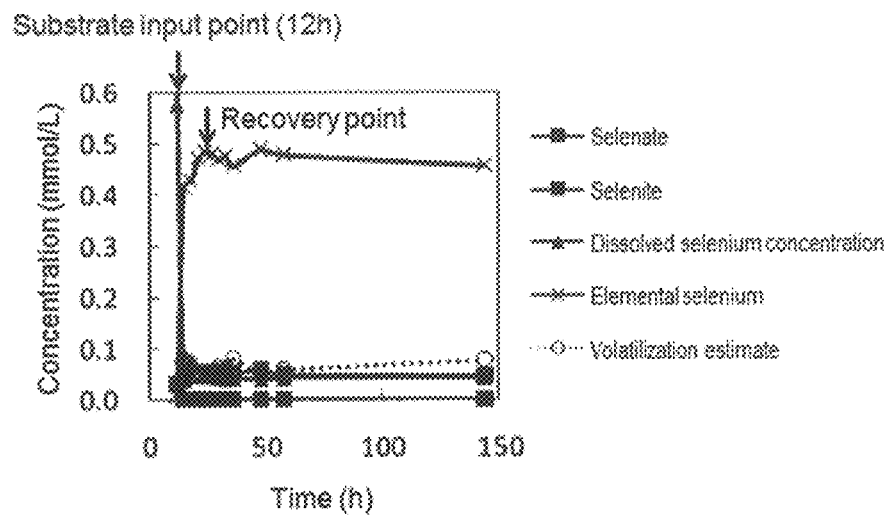
[Fig. 38]
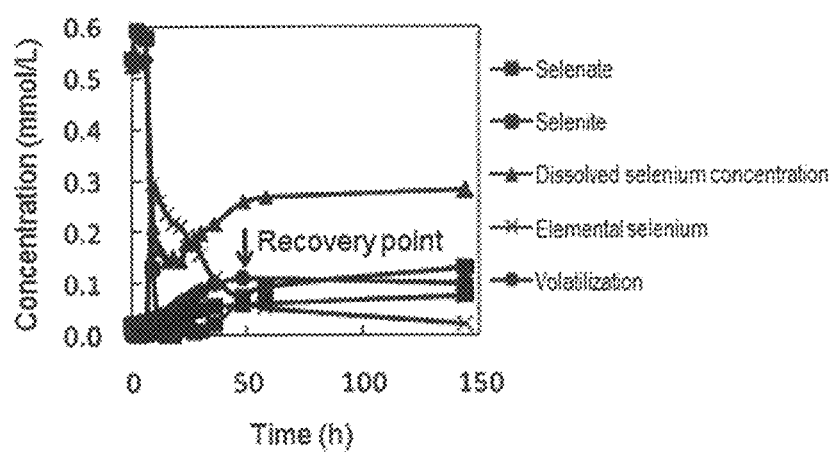

[Fig. 39]
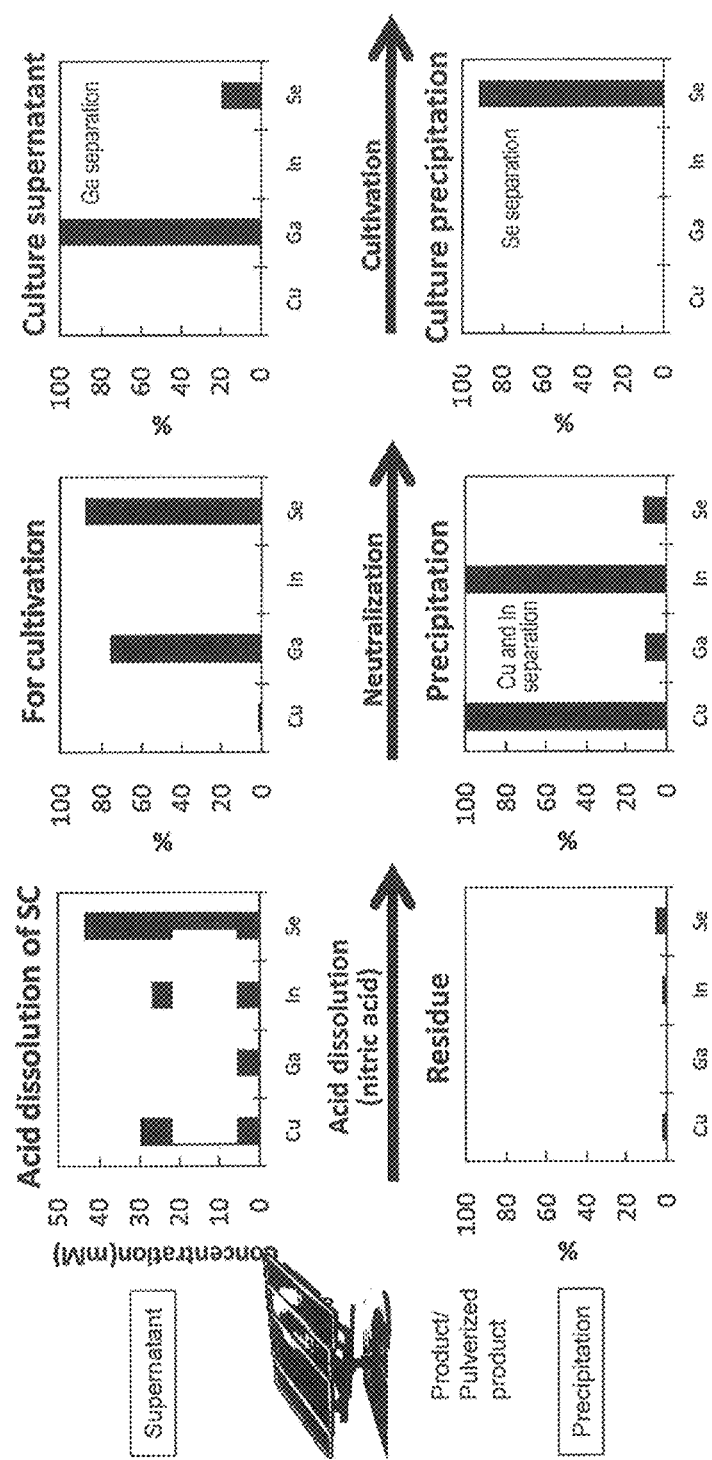

[Fig. 40]
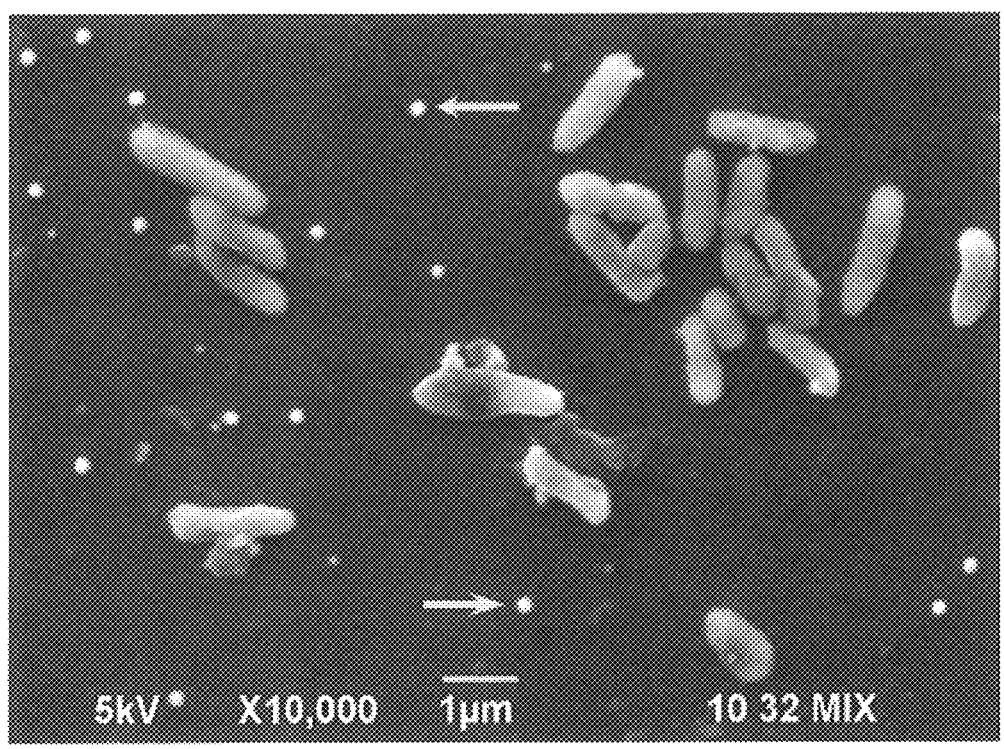

[Fig. 41]
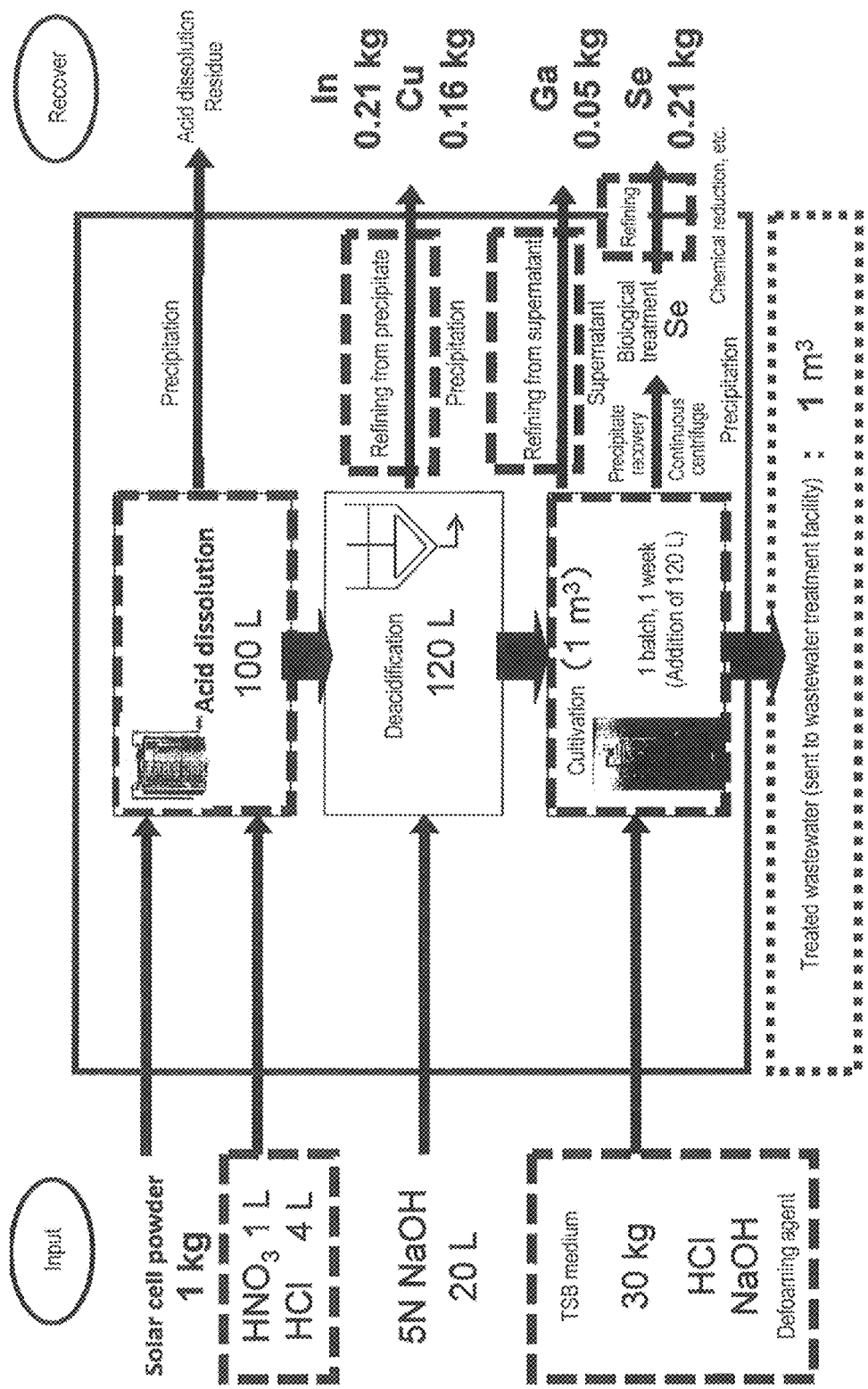

METHOD FOR RECOVERING SELENIUM

TECHNICAL FIELD

The present invention relates to a method for recovering selenium from wastewater/waste and the like using a microorganism.

BACKGROUND ART

Japan is the world's largest selenium producer. Japan exports 80% of its production of selenium. Selenium is mainly obtained as a by-product from copper electrolytic slime that is generated upon copper refining. Produced selenium is used in the fields of, for example, glasses, colors, and chemicals. It is said that eventually 6 t of selenium is discharged into water systems. Oxyanions, which are in the form of soluble selenate and selenite, have chronic/acute toxicity to organisms. Therefore, a strict uniform wastewater standard is set at 0.1 mg/L. At present, wastewater is cleaned by coagulation precipitation or chelate treatment; however, such treatment is problematic because of high cost. In these methods, resources are largely consumed and selenium cannot be recovered as a resource from chemical sludge or the like because of the low selenium content.

Non-Patent Literature 1 discloses reduction of selenate and selenite by means of *Pseudomonas stutzeri*. In addition, the present inventors isolated *Pseudomonas stutzeri* NT-I with an aim to develop a biological treatment method for a selenium compound (Patent Literature 1). *Pseudomonas stutzeri* NT-I is capable of efficiently reducing selenate into selenite and further reducing selenite into elemental selenium. Elemental selenium is water-insoluble and atoxic. Therefore, it would be possible to detoxify, for example, wastewater containing a selenium compound at relatively low cost and recover selenium from the detoxified product for recycling selenium with the use of *Pseudomonas stutzeri* NT-I. It is necessary to examine treatment conditions and develop facilities in order to carry out treatment of a selenium compound using a microorganism to efficiently recover selenium.

PRIOR ART DOCUMENTS

Patent Documents

Patent Document 1: JP 2010-142166 A

Non-Patent Documents

Non-Patent Document 1: L. Lortie et al., Applied and Environmental Microbiology, 58(12), 1992, pp. 4042-4044

SUMMARY OF INVENTION

Problem to be Solved by the Invention

An object of the present invention is to provide a method for efficiently recovering solid selenium or gaseous selenium from wastewater/waste using a microorganism.

Means for Solving the Problem

In order to achieve the above object, the present inventor conducted experiments for recovering selenium from selenium-containing wastewater or waste in a culture system employing a jar fermenter and examined methods for pretreating actual selenium-containing wastewater or waste (dilution, input time, dissolution, and neutralization), culture methods for recovering selenium or gaseous selenium, and aftertreatment methods (acid dissolution, activated carbon adsorption, and centrifugation). As a result, the present inventor found that selenium can be efficiently recovered by treating wastewater/waste under certain conditions using *Pseudomonas stutzeri* NT-I. This has led to the completion of the present invention.

The present invention relates to the following embodiments.

(1) A method for recovering selenium, comprising reducing a water-soluble selenium compound so as to produce elemental selenium or gaseous selenium by allowing a sample containing a water-soluble selenium compound to come into contact at a temperature which is more than 35° C. and is 40° C. or less at pH 7.0 to 9.4 with a microorganism capable of producing elemental selenium or gaseous selenium through reduction of a water-soluble selenium compound.

(2) The method for recovering selenium according to claim 1, wherein the microorganism capable of producing elemental selenium or gaseous selenium through reduction of a water-soluble selenium compound is an aerobic microorganism.

(3) The method for recovering selenium according to claim 1 or 2, wherein the microorganism capable of producing elemental selenium or gaseous selenium through reduction of a water-soluble selenium compound is a bacterium belonging to the genus *Pseudomonas*.

(4) The method for recovering selenium according to any one of claims 1 to 3, wherein the microorganism capable of producing elemental selenium or gaseous selenium through reduction of a water-soluble selenium compound is *Pseudomonas stutzeri*.

(5) A method for recovering selenium, comprising reducing a water-soluble selenium compound so as to produce elemental selenium or gaseous selenium by allowing a sample containing a water-soluble selenium compound to come into contact at a temperature of 35° C. to 40° C. and at pH 7.0 to 9.4 with *Pseudomonas stutzeri* NT-I (Accession No. NITE BP-685) serving as a microorganism capable of producing elemental selenium or gaseous selenium through reduction of a water-soluble selenium compound.

(6) The method according to any one of (1) to (5), wherein the water-soluble selenium compound is selenate or selenite.

(7) The method according to any one of (1) to (6), wherein the sample containing a water-soluble selenium compound is allowed to come into contact with the microorganism capable of producing elemental selenium or gaseous selenium through reduction of a water-soluble selenium compound under aeration conditions.

(8) The method according to (7), wherein the aeration conditions include 1 L/minute to 5 L/minute.

(9) The method according to (7) or (8), wherein the sample containing a water-soluble selenium compound is allowed to come into contact with the microorganism capable of producing elemental selenium or gaseous selenium through reduction of a water-soluble selenium compound under conditions in which aeration is conducted and then stopped.

(10) The method according to any one of (1) to (9), wherein the sample containing a water-soluble selenium com- pound is allowed to come into contact with the microorganism capable of producing elemental selenium or gaseous selenium through reduction of a water-soluble selenium compound under stirring conditions.

(11) The method according to (10), wherein the stirring conditions include a stirring rate of 250 rpm or less.

(12) The method according to any one of (1) to (11), wherein the sample containing a water-soluble selenium compound has a selenium concentration of 100 to 6000 μmol/L.

(13) The method according to any one of (1) to (12), wherein the sample containing a water-soluble selenium compound is a sample obtained by pretreating a selenium-containing material.

(14) The method according to (13), wherein the sample containing a water-soluble selenium compound is a sample obtained by dissolving a selenium-containing material in inorganic acid.

(15) The method according to (13) or (14), wherein the sample containing a water-soluble selenium compound is a sample obtained by dissolving a selenium-containing material in inorganic acid and adding an alkaline aqueous solution for neutralization.

(16) The method according to any one of (13) to (15), wherein the selenium-containing material is a material containing copper (Cu), indium (In), and selenium (Se).

(17) The method according to any one of (13) to (16), wherein the selenium-containing material is a material containing copper (Cu), indium (In), gallium (Ga), and selenium (Se).

(18) The method according to any one of (13) to (17), wherein the selenium-containing material is a panel material.

(19) The method according to any one of (13) to (18), wherein the selenium-containing material is a solar cell panel.

(20) A method for recovering selenium, comprising reducing a water-soluble selenium compound so as to produce elemental selenium or gaseous selenium by allowing a sample containing a water-soluble selenium compound obtained by pretreating a material containing copper (Cu), indium (In), and selenium (Se) to come into contact with a microorganism capable of producing elemental selenium or gaseous selenium through reduction of a water-soluble selenium compound.

(21) The method for recovering selenium according to (20), wherein the microorganism capable of producing elemental selenium or gaseous selenium through reduction of a water-soluble selenium compound is an aerobic microorganism.

(22) The method for recovering selenium according to (20) or (21), wherein the microorganism capable of producing elemental selenium or gaseous selenium through reduction of a water-soluble selenium compound is a bacterium belonging to the genus *Pseudomonas*.

(23) The method according to any one of (20) to (22), wherein the microorganism capable of producing elemental selenium or gaseous selenium through reduction of a water-soluble selenium compound is *Pseudomonas stutzeri*.

(24) The method according to any one of (20) to (23), wherein the microorganism capable of producing elemental selenium or gaseous selenium through reduction of a water-soluble selenium compound is *Pseudomonas stutzeri* NT-I (Accession No. NITE BP-685).

(25) The method according to any one of (20) to (24), wherein the material containing copper (Cu), indium (In), and selenium (Se) further contains gallium (Ga).

(26) The method according to any one of (20) to (25), wherein the sample containing a water-soluble selenium compound is obtained by dissolving the material containing copper (Cu), indium (In), and selenium (Se) in inorganic acid.

(27) The method according to any one of (20) to (26), wherein the sample containing a water-soluble selenium compound is obtained by dissolving the material containing copper (Cu), indium (In), and selenium (Se) in inorganic acid and adding an alkaline aqueous solution for neutralization.

(28) A method for recovering copper (Cu), indium (In), selenium (Se), and gallium (Ga), comprising:
dissolving a material containing copper (Cu), indium (In), selenium (Se), and gallium (Ga) in inorganic acid;
adding an alkaline aqueous solution for neutralization so as to recover copper (Cu) and indium (In) as precipitates and a supernatant containing selenium (Se) and gallium (Ga); and
reducing a water-soluble selenium compound so as to recover elemental selenium as a precipitate and gallium (Ga) as a supernatant by allowing the supernatant containing selenium (Se) and gallium (Ga) to come into contact with a microorganism capable of producing elemental selenium or gaseous selenium through reduction of a water-soluble selenium compound.

Advantageous Effects of Invention

According to the present invention, selenium can be efficiently recovered by treating wastewater/waste with the use of microorganisms.

BRIEF DESCRIPTION OF DRAWINGS

FIG. 1 shows the temporal changes in reduction of selenate and selenite by the NT-I strain during jar fermenter culture (38° C., no pH adjustment (initial pH 7.0), 1 L/min, 120 rpm).

FIG. 2 shows the temporal changes in the number of cells of the NT-I strain in a cell growth system employing a jar fermenter (38° C., pH 9.0, 1 L/min, 250 rpm).

FIG. 3 shows the relationship between the number of cells and $O.D._{600}$ of the NT-I strain.

FIG. 4 shows the temporal changes in reduction of selenate reduction by the NT-I strain during jar fermenter culture (38° C., no pH adjustment (initial pH 7.0), 1 L/min, 120 rpm).

FIG. 5 shows the influence of pH on reduction of selenate by the NT-I strain during jar fermenter culture.

FIG. 6 shows the results of examining the optimal pH in a selenate reduction reaction of the NT-I strain during jar fermenter culture.

FIG. 7 shows the influence of pH on reduction of selenite by the NT-I strain during jar fermenter culture.

FIG. 8 shows the results of examining the optimal pH in a selenite reduction reaction of the NT-I strain during jar fermenter culture.

FIG. 9 shows the influence of temperatures on reduction of selenate by the NT-I strain during jar fermenter culture.

FIG. 10 shows the results of examining the optimal temperature in a selenate reduction reaction of the NT-I strain during jar fermenter culture.

FIG. 11 shows the influence of temperatures on reduction of selenite by the NT-I strain during jar fermenter culture.

FIG. 12 shows the results of examining the optimal temperature in a selenite reduction reaction of the NT-I strain during jar fermenter culture.

FIG. 13 shows the influence of aeration volumes on reduction of selenate by the NT-I strain and growth of the strain during jar fermenter culture.

FIG. 14 shows the results of examining aeration volumes in a selenate reduction reaction of the NT-I strain during jar fermenter culture.

FIG. 15 shows the influence of stirring rates on reduction of selenate by the NT-I strain and growth of the strain during jar fermenter culture.

FIG. 16 shows the results of examining stirring rates in a selenate reduction reaction of the NT-I strain during jar fermenter culture.

FIG. 17 shows the relationship between the stirring rates and dissolved oxygen (DO) in a selenate reduction reaction of the NT-I strain during jar fermenter culture.

FIG. 18 shows the influence of aeration volumes on reduction of selenite by the NT-I strain and growth of the strain during jar fermenter culture.

FIG. 19 shows the relationship between the stirring rates and dissolved oxygen (DO) in a selenite reduction reaction of the NT-I strain during jar fermenter culture.

FIG. 20 shows the influence of aeration on selenite reduction.

FIG. 21 shows reduction under optimal conditions for the NT-I strain during jar fermenter culture.

FIG. 22 shows the influence of aeration on the decrease in elemental selenium.

FIG. 23 shows the GC-MS results for the gas phase during jar fermenter culture.

FIG. 24 shows the measurement results of GC-MS performed after an equilibrium reaction between DMDSe and DMDS (A: total ion chromatography; B: filtering by DMDS (MW:94), DMDSe (MW:142), and DMSSe (MW:190)).

FIG. 25 shows changes in the selenium concentration of each phase under optimal reduction conditions.

FIG. 26 shows the results of gaseous selenium recovery by activated carbon (38° C., pH 9.0, 1 L/min, 250 rpm, 48 h).

FIG. 27 shows the results of examining recovery of highly concentrated solid selenium.

FIG. 28 shows the results of solid recovery from wastewater at 38° C., pH 9, 250 rpm, and 0 L/min (1 L/min up to 12 h).

FIG. 29 shows the results of gas recovery from wastewater at 38° C., pH 9, 250 rpm, and 1 L/min.

FIG. 30 shows the results of solid recovery from a solution sample 1 at 38° C., pH 9, 250 rpm, and 0 L/min (1 L/min up to 12 h).

FIG. 31 shows changes in the nitrate/nitrite concentration upon solid recovery from a solution sample 1 at 38° C., pH 9, 250 rpm, and 0 L/min (1 L/min up to 12 h).

FIG. 32 shows the results of solid recovery from a neutralized solution sample at 38° C., pH 9, 250 rpm, and 0 L/min (1 L/min up to 12 h).

FIG. 33 shows the results of gas recovery from a solution sample 1 at 38° C., pH 9, 250 rpm, and 1 L/min.

FIG. 34 shows changes in the nitrate/nitrite concentration upon gas recovery from a solution sample 1 at 38° C., pH 9, 250 rpm, and 1 L/min.

FIG. 35 shows the results of gas recovery from a solution sample 2 at 38° C., pH 9, 250 rpm, and 1 L/min.

FIG. 36 shows the results of gas recovery from a neutralized solution sample at 38° C., pH 9, 250 rpm, and 1 L/min.

FIG. 37 shows the results of solid recovery from waste containing Se at 38° C., pH 9, 250 rpm, and 0 L/min (1 L/min up to 12 h).

FIG. 38 shows the results of gas recovery from waste containing Se at 38° C., pH 9, 250 rpm, and 1 L/min.

FIG. 39 shows the summary of rare metal recovery with the use of a powder sample obtained from a CIGS solar panel in a culture system employing a jar fermenter.

FIG. 40 shows a photograph of produced elemental selenium.

FIG. 41 shows the estimates of the amounts of rare metals recovered from the CIGS solar cell powder.

EMBODIMENTS FOR CARRYING OUT THE INVENTION

Embodiments of the present invention are described below.

The term "water-soluble selenium compound" refers to a water-soluble compound containing selenium. Examples of a water-soluble selenium compound include selenate and selenite.

The term "elemental selenium" refers to elemental selenium which is not in the form of a compound comprising different element(s).

The term "gaseous selenium" refers to a selenium compound that can be recovered in the form of gas. Examples of gaseous selenium include dimethyl diselenide and dimethyl selenide.

According to the treatment method of the present invention, a microorganism capable of producing elemental selenium or gaseous selenium through reduction of a water-soluble selenium compound is used. The type of the above microorganism is not particularly limited as long as the microorganism is capable of producing elemental selenium or gaseous selenium through reduction of a water-soluble selenium compound. Examples thereof include bacteria, yeast, protozoa, fungi, and molds. The microorganism capable of producing elemental selenium or gaseous selenium through reduction of a water-soluble selenium compound is preferably an aerobic microorganism and more preferably an aerobic bacterium. The microorganism used in the present invention is further preferably a bacterium belonging to the genus *Pseudomonas* and particularly preferably *Pseudomonas stutzeri*.

An example of *Pseudomonas stutzeri* that can be used is *Pseudomonas stutzeri* NT-I (hereinafter sometimes referred to as "the NT-I strain"). The NT-I strain is a microorganism which was isolated for the first time by the present inventors from wastewater at the bottom of wastewater drains in a metal recycling plant. Physiological characteristics of the NT-I strain are described below. The nucleotide sequence of 16SrDNA of the NT-I strain was found to be 100% identical to the nucleotide sequence of 16SrDNA of *Pseudomonas stutzeri* DSM 5190. Based on these results, the NT-I strain was classified as corresponding to *Pseudomonas stutzeri*. The NT-I strain was deposited on Dec. 4, 2008 with Patent Microorganisms Depositary, National Institute of Technology and Evaluation (2-5-8 Kazusakamatari, Kisarazu, 292-0818, Chiba, Japan) as Identification No. NT-I SIID6937 and Accession No. NITE P-685 (Patent Document 1). The strain deposited as Accession No. NITE P-685 was transferred on Jan. 30, 2012 from the original depositary to an international depository as Accession No. NITE BP-685 under the Budapest Treaty. *Pseudomonas stutzeri* NT-I (Accession No. NITE BP-685) is known as having selenate reduction activity and selenite reduction activity. Selenate reduction activity can be measured by quantitatively determining selenite produced from selenate. Selenite reduction activity can be measured by quantitatively determining elemental selenium produced from selenite.

| Test item | Results |
|---|---|
| Form | Bacillary form |
| Colony color | White (TBS medium) |
| Gram stainability | − |
| Motility | + |
| O-F test | O |
| Catalase activity | + |
| Oxidase activity | + |

The NT-I strain can grow under aerobic conditions and can reduces a water-soluble selenium compound. This feature is advantageous in terms of the ease of handling, high reaction rates, stability of treatment performance, and so on.

According to the present invention, a sample containing a water-soluble selenium compound is allowed to come into contact with the microorganism capable of producing elemental selenium or gaseous selenium through reduction of a water-soluble selenium compound at a temperature which is more than 35° C. and is 40° C. or less at pH 7.0 to 9.4. Thus, it is possible to produce elemental selenium or gaseous selenium through reduction of the water-soluble selenium compound.

Preferably, a sample containing a water-soluble selenium compound is allowed to come into contact with *Pseudomonas stutzeri* NT-I (Accession No. NITE BP-685) at a temperature of 35° C. to 40° C. and at pH 7.0 to 9.4. Thus, it is possible to produce elemental selenium or gaseous selenium through reduction of the water-soluble selenium compound.

The temperature is not particularly limited as long as it is in a range which is more than 35° C. and is 40° C. or less (35° C. to 40° C. for *Pseudomonas stutzeri* NT-I) without particular limitations. However, it is preferably 36° C. to 40° C., more preferably 37° C. to 39° C., and most preferably approximately 38° C. The pH is not particularly limited as long as it is pH 7.0 to 9.4. However, it is preferably 7.0 to 9.0, more preferably 8.0 to 9.0, and most preferably approximately 9.0.

Preferably, it is possible to allow the sample containing a water-soluble selenium compound to come into contact with the microorganism capable of producing elemental selenium or gaseous selenium through reduction of a water-soluble selenium compound under aeration conditions. The aeration conditions are not particularly limited; however, the aeration rate is preferably 1 L/minute to 5 L/minute. It is also possible to allow the sample containing a water-soluble selenium compound to come into contact with the microorganism capable of producing elemental selenium or gaseous selenium through reduction of a water-soluble selenium compound under conditions in which aeration is conducted in the above manner and then stopped.

More preferably, it is possible to allow a sample containing a water-soluble selenium compound to come into contact with the microorganism capable of producing elemental selenium or gaseous selenium through reduction of a water-soluble selenium compound under stirring conditions. Stirring conditions are not particularly limited; however, the stirring rate is preferably 250 rpm or less.

A toxic water-soluble selenium compound can be removed as a low-toxic volatile selenium compound from soil or wastewater by the method of the present invention. In addition, selenium can be recovered/recycled by making use of dimethyl diselenide obtained by the method of the present invention for selenium refining or the like. For example, when dimethyl diselenide obtained by the method of the present invention is introduced into a furnace which is used for conventional selenium refining, methyl groups are removed in the form of carbon dioxide such that the resulting selenium dioxide can be recovered by a scrubber.

When the microorganism capable of producing elemental selenium or gaseous selenium through reduction of a water-soluble selenium compound is cultivated in the presence of selenate, it is observed that selenite, elemental selenium, and gaseous selenium (dimethyl diselenide) are produced over time. In one embodiment, the period required to cultivate the microorganism capable of producing elemental selenium or gaseous selenium through reduction of a water-soluble selenium compound for the purpose of treating a 1 mM water-soluble selenium compound by the method of the present invention is, for example, 1 hour or more, preferably 5 hours or more, more preferably 15 hours or more, and further preferably 20 hours or more. For instance, the period is 20 days or less, preferably 15 days or less, more preferably 10 days or less, and further preferably 5 days or less.

The present invention is more specifically described with reference to the following Examples. However, the present invention is not limited to the Examples.

EXAMPLES

Example 1

Se Reduction/Volatilization Characteristics in a Bioreactor System

In Example 1, optimal conditions for reduction of selenate and selenite in a bioreactor system were examined.
(1) Experimental Materials and Method
(1-1) Culture Method TSB medium (3000 ml) was introduced into a 5-L volume jar fermenter (Bioneer-C500N 5L(S), B. E. Marubsishi Co., Ltd.) and subjected to autoclave treatment. A 500 mmol/L selenate solution or selenite solution (3 ml) was added to the medium. Cells were harvested by centrifuging a culture solution obtained through 12-hour preculture and a cell suspension was adjusted to $OD_{660}$=1.0. Thereafter, the medium was inoculated with 30 ml (1%) of the cell suspension. Culture was carried out under different culture conditions.

(1-2) Sampling and Preparation of Measurement Samples

An adequate amount of the culture solution was collected from the jar fermenter to measure cell turbidity ($O.D._{600}$). A portion (2 ml) of the culture solution was collected and centrifuged at 15,000 rpm for 5 minutes. After centrifugation, a sample obtained by filtrating the supernatant (filter size: 0.2 μm) was designated as a supernatant sample. A pellet obtained via centrifugation was designated as a precipitation sample.

(1-3) Measurement of the Concentrations of Selenate and Selenite

A portion (100 μl) of the above supernatant sample was collected and diluted to one tenth (1/10) of the original concentration with ultrapure water (900 μl). The diluted solution was subjected to ion chromatography (ICS-1100; detector: DS6 HEATED CONDUCTIVITY CELL; column: IonPac AS12A; guard column: AG12A; suppressor: ASRS300; eluent: 3.0 mM $Na_2CO_3$; flow rate: 1.5 ml/min; Dionex Co., Ltd.) so as to measure the concentrations of selenate and selenite.

(1-4) Measurement of the Dissolved Selenium Concentration

A portion (1000 μl) of the supernatant sample was added to ultrapure water (8900 μl) supplemented with concentrated nitric acid (100 μl) so as to be diluted to one tenth (1/10) of the original concentration. The resulting solution was designated as a measurement sample. The total selenium concentration was measured by ICP-AES (iCAP 6300 Duo, Thermo Fisher Scientific K.K.).

(1-5) Measurement of the Elemental Selenium Concentration

Ultrapure water (2 ml) was added to the precipitation sample. The resultant was washed by vortexing and then centrifuged to recover a precipitate. After washing was repeatedly carried out, concentrated nitric acid (1500 μl) and concentrated sulfuric acid (50 μl) were added to the precipitation sample and a precipitate was dissolved by vortexing.

The precipitate-dissolved solution was centrifuged at 15,000 rpm for 5 minutes so as to be separated into a supernatant and a precipitate. A portion of the supernatant solution was introduced into a 10-ml measuring flask. The precipitate was dissolved again under the same conditions. A supernatant was collected therefrom and a portion thereof was introduced into the measuring flask containing the supernatant solution. Ultrapure water was added to the 10-ml measuring flask to a level of the marked line. The measured sample was designated as a measurement sample. The measurement sample was subjected to measurement of the selenium concentration by ICP-AES.

(1-6) Gas Recovery

A Pharmed tube was connected to an exhaust port of the jar fermenter for bubbling into concentrated nitric acid (150 ml) in a 250-ml volume reagent bottle. Air stone was connected to a face of the tube which was in contact with concentrated nitric acid. Concentrated nitric acid was sampled in a time-dependent manner. The selenium concentration was measured by ICP-AES.

(1-7) Correlation Between the Number of Viable Cells and Cell Turbidity (O.D.$_{600}$)

In order to calculate the rate of reduction per bacterial cell of the NT-I strain, the number of cells of the NT-I strain was counted and O.D.$_{600}$ was measured in a time-dependent manner in order to determine a correlation therebetween.

A jar fermenter was used for culture. Culture was carried out by a culture method (2.1) at 38° C., pH 9.0, 1 L/min, and 250 rpm. After the beginning of the experiment, a culture solution was collected in a time-dependent manner to count the number of cells and measure O.D.$_{600}$. The average of the number of cells was obtained by counting the number of cells in 60 grids of a counting chamber using a phase-contrast microscope (DM1000, Laica). A spectrophotometer (V-600, JASCO Corporation) was used for measurement of O.D.$_{600}$.

(2) Experimental Results and Discussions (2-1) Reduction Characteristics in a Jar Fermenter FIG. 1 shows the results of culture under the following culture conditions: 38° C., no pH adjustment (initial pH 7.0), 1 L/min, and 120 rpm. FIG. 1 shows, as examples of typical temporal changes, characteristics of selenate and selenite reduction by the NT-I strain during culture in a jar fermenter. As a result of the addition of 0.5 mM selenate, selenate reduction begun after an induction phase (approximately 2 hours). Then, all selenate was reduced within 4 hours, and accumulating selenite completely disappeared in the culture solution within 22 hours. In a similar experiment using an Erlenmeyer flask, selenate is reduced within 10 hours, and selenite is reduced within 16 hours. In view of this, it can be concluded that selenate reduction was accelerated and selenite reduction was decelerated under the above culture conditions compared with the case of the experiment in an Erlenmeyer flask.

Accumulation of elemental selenium as a result of selenite reduction takes place at a level of 0.1 mmol/L or less at a maximum. In other words, the recovery rate of solid Se is 20% or less. Since substantially no dissolved selenium was detected in the solution, it is considered that the transition from elemental selenium to gaseous Se very rapidly proceeded in this Example.

(2-2) Correlation Between the Number of Viable Cells and Cell Turbidity (O.D.$_{600}$)

FIG. 2 shows temporal changes in the number of cells of the NT-I strain in a cell growth system employing a jar fermenter. The results indicate that the logarithmic growth phase of the NT-I strain is approximately 7 hours and then cell growth reaches the stationary phase. The results also indicate that the O.D.$_{600}$ value increases as the growth of the NT-I strain proceeds (FIG. 3).

The number of cells was calculated based on the O.D.$_{600}$ value using the proportionality coefficient obtained in this Example.

(2-3) Calculation of the Specific Reduction Rate

In order to evaluate the relationship between changes under different culture conditions and the selenate reduction rate, the amount of selenate reduced per unit of time for each variable was calculated as the selenate reduction rate (mmol/cell/hr). As an example, FIG. 4 shows temporal changes in the selenate concentration under the following culture conditions: 38° C., no pH adjustment (initial pH 7.0), 1 L/min, and 120 rpm. First, a gradient (mmol/3 L/hr) of the selenate reduction rate (mmol/cell/hr) was obtained in a period in which the selenate concentration decreased in a linear manner. Further, the number of cells (cell/ml) was calculated based on the O.D.$_{600}$ value before and after the calculation of the selenium reduction rate. The selenate reduction rate (mmol/cell/hr) was calculated by dividing the gradient by the number of cells. Also, the selenite reduction rate was calculated in a similar manner.

(2-4) Influence of pH on Reduction of Selenate and Selenite

The existing findings revealed that the NT-I strain can grow within a pH range of 6.0-9.0 and that the optimal pH for the growth is 7.0. Therefore, the influence of pH on reduction of selenate and selenite by the NT-I strain was examined in this Example.

Regarding selenate reduction, it was found that 0.5 mmol/L selenate can be reduced at pH 6.5-9.0 for 4-5 hours (FIG. 5). In addition, reduction of selenate was observed at pH 10.0 after 60 hours (data not shown), although the growth was very slow. FIG. 6 shows the results of the calculation of the specific reduction rate per bacterial cell. The results indicate that the optimal pH for reduction of selenate by the NT-I strain during jar fermenter culture is pH 7.5-8.0.

For reduction of selenite, culture was carried out with the addition of 0.5 mmol/L selenite as a substrate. As a result, it was found that selenite can be reduced at pH 7.0-9.0 within 24 hours (FIG. 7). In particular, it was found that the reduction rate at pH 9.0 is very fast such that selenite can be reduced within 15 hours. The specific reduction rate per bacterial cell was calculated. Activity was substantially the same at pH 7.0-8.5; however, the specific reduction rate at pH 9.0 was twice or more than that at pH 7.0-8.5 (FIG. 8). In a conventional experiment using an Erlenmeyer flask, the optimal pH is 7.0. However, it was found that selenite is very rapidly reduced when the pH is maintained at 9.0 in the case of jar fermenter culture.

(2-5) Influence of Temperatures on Reduction of Selenate and Selenite

It has been revealed that the NT-I strain can grow at 10° C.-42° C. and the optimal temperature for the growth is 38° C. Thus, an optimal reduction test was conducted at 30° C.-40° C. for jar fermenter culture.

As a result, it was found that selenate is reduced at 30° C.-40° C. within 5 hours (FIG. 9). In particular, selenate disappeared at 38° C. within 4 hours, which was the shortest time. The specific reduction rate was calculated. The obtained specific reduction rate was high at 35° C.-38° C. (FIG. 10). These results indicate that the optimal temperature for reduction of selenate is 38° C.

For reduction of selenite, culture was carried out with the addition of 0.5 mmol/L, selenite as a substrate. It was found that selenite is reduced at 30° C.-40° C. within 18 hours (FIG. 11). Selenite reduction at 38° C. ended within 15 hours, which was the shortest time. As a result of the calculation of the specific reduction rate, the obtained rate was high at 30° C.-38° C. and substantially comparable to the above rate (FIG. 12). These results indicate that the optimal temperature for selenite reduction is 38° C.

(2-6) Influence of Aeration/Stirring on Selenate

Factors that influence the oxygen transfer rate upon reduction of selenate/selenite by the NT-I strain have not been examined in conventional experiments of culture in an Erlenmeyer flask or the like. The reduction reaction of the NT-I strain is very interesting because a reduction reaction which is originally an anaerobic reaction rapidly proceeds under aerobic conditions. Therefore, aeration and stirring upon jar fermenter culture were examined.

FIG. 13 shows the influence of changes in the aeration volume for reduction of selenate. The results indicate that reduction of selenate rapidly proceeds within 4 hours at an aeration volume of 0-5 L/min. The selenate concentration at 3 hours increases as the aeration volume increases. The number of cells, i.e., the growth rate, increases as the aeration volume increases. At an aeration volume of 0 L/min, the growth of bacterial cells was remarkably suppressed. Regarding a comparison in terms of the specific reduction rate, the reduction rate was found to be substantially stable; however, the specific reduction rate at 0 L/min increased since the number of cells was suppressed (FIG. 14). These results indicate that the NT-I strain would have a high reduction capacity because selenate reduction does not depend on the number of cells and thus the reduction rapidly proceeds even with a small amount of bacterial cells. Meanwhile, the time point of the beginning of selenate reduction is always 2 hours or more. Thus, there is a probability that other factors influence the beginning of reduction.

Next, FIG. 15 shows influence of stirring on selenate reduction. The results show that selenate reduction rapidly proceeds at 120-200 rpm within 5 hours. When the involvement of the specific reduction rate in the stirring rate is shown in chart form, it is understood that the specific reduction rate increases inversely proportional to the stirring rate (FIG. 16). Further, selenate is substantially completely reduced at 250 rpm within 6 hours. Meanwhile, selenate reduction is obviously suppressed at 300 rpm. In this case, although approximately a half of selenate is reduced within 9 hours, selenate reduction does not further proceed (data not shown). Since the growth of bacterial cells is promoted proportional to the stirring rate, it is considered that selenate reduction is influenced by other factors other than the number of cells (FIG. 15).

(2-7) Correlation Between Selenate Reduction and Dissolved Oxygen (DO)

In order to examine the influence of stirring on the rate of oxygen transfer in medium, dissolved oxygen (DO) and selenate reduction were compared (FIG. 17). A comparison of the charts in FIG. 17 shows that selenate reduction starts to proceed after DO reaches 0%. Since a reduction reaction is originally a reaction that proceeds under anaerobic conditions, it is considered that the growth of bacterial cells causes consumption of oxygen in a culture solution, which results in microanaerobic conditions that allow selenate reduction to subsequently proceed. DO increases in the course of selenate reduction at 300 rpm, and at the same time, selenate reduction is discontinued. Therefore, it is considered that when DO decreases to 0%, selenate reduction proceeds, and when DO increases from 0%, selenate reduction does not proceed.

(2-8) Influence of Aeration/Stirring on Selenite

FIG. 18 shows the influence of changes in the stirring rate on selenite reduction. The results indicate that selenite reduction rapidly proceeds at 120-400 rpm within 15 hours. In particular, selenite was found to have disappeared at 300 rpm within 12 hours, which was the shortest time. Regarding the increase in the number of cells, it is understood that the growth of bacterial cells proceeds rapidly at 300 rpm; however, an induction phase is prolonged at 400 rpm, although the growth rate of bacterial cells is fast at 400 rpm. These results indicate that the optimal stirring rate for selenite reduction is 300 rpm.

FIG. 19 shows a comparison between dissolved oxygen (DO) and selenite reduction. At 120-300 rpm, selenite reduction proceeds after DO decreases. The decrease in DO is considered to be influenced by the growth of bacterial cells, which is understood from the growth curve in FIG. 19. Therefore, it is considered that selenite reduction proceeds in a state in which the number of cells has increased to a certain level. Meanwhile, the results obtained at 400 rpm show that selenite reduction proceeds even in a state in which DO does not decrease to 0%. Therefore, it can be said that a condition that causes DO to decrease to 0% is not a necessary condition for selenite reduction.

FIG. 20 shows the results obtained after culture of the NT-I strain for 12 hours under optimal reduction conditions and the subsequent addition of selenate in a case in which aeration was maintained at 1 L/min and those in a case in which aeration was changed to 0 L/min to stop aeration. It was found that selenite is produced immediately after the addition of selenate and then selenite reduction proceeds in both cases. The rate of selenite reduction was calculated. As a result, it was found that when aeration was conducted, the rate was $9.6 \times 10^{-18}$ mol/cell/hr, and when aeration was stopped, the rate was $3.8 \times 10^{-18}$ mol/cell/hr, indicating that aeration promotes selenite reduction to result in an approximately 2.5 times increase in the reduction rate (FIG. 20B). These results suggest that selenite reduction is a reaction in which oxygen is consumed.

(2-9) Summary of Optimization of Reduction of Selenate and Selenite

Table 1 summarizes optimal conditions for reduction of selenate and selenite. Under conditions before optimization (38° C., no pH adjustment, 120 rpm, 1 L/min), selenate reduction ended within 4 hours, while it took 22 hours for selenite reduction to end (FIG. 1). That is, reduction of selenate into elemental selenium depends on the rate of selenite reduction. Therefore, conditions that do not inhibit selenate reduction and optimize selenite reduction were determined to be optimal conditions for selenium oxyanion reduction.

It is also possible to use a culture method where culture conditions are switched during culture, wherein the optimal conditions for selenate reduction and the optimal conditions for selenite reduction are employed as the optimal conditions for selenium oxyanion reduction. However, for example, the influence of uncertain factors such as contamination with impurities makes the selenate reduction time unclear when actual waste or wastewater is treated. Also, it is difficult to perform real-time monitoring because measurement of selenate takes nearly 30 minutes. For such reasons, culture conditions were determined on the condition that the initial setting conditions be maintained.

FIG. 21 shows the results of culture under the optimal conditions for selenium oxyanion reduction in consideration of the summary of the above results. Compared with culture before optimization of the reduction conditions (FIG. 1), the time for the completion of reduction of selenate into selenite was shortened from 22 hours to 7 hours, which corresponds to a decrease to one third (⅓) of the time before optimization. Also, the concentration of elemental selenium was observed to have increased as selenite reduction proceeded. Thereafter, the produced elemental selenium rapidly decreased. This probably means that production of gaseous selenium rapidly proceeded. Culture for production of gaseous selenium from elemental selenium is examined in Example 2 below.

TABLE 1

Optimal conditions for reduction of oxyanions

|  | Temperature (° C.) | pH | Stirring (rpm) |
|---|---|---|---|
| Selenate reduction | 38 | 7.5-8.0 | 150 |
| Selenite reduction | 38 | 9.0 | 300 |
| Optimal conditions for selenium oxyanion reduction | 38 | 9.0 | 250 |

*: Aeration volume: 1 L/min

Example 2

Examination of Se Volatilization/Recovery Process in a Laboratory-Scale Reactor

It is an important point to control production of gaseous selenium in order to improve the recovery rate of solid selenium. In view of this, for the purpose of establishing an Se recovery process using a microorganism, a method for recovering gaseous selenium and a method for controlling production of gaseous selenium were examined to realize solid selenium recovery and gaseous selenium recovery in Example 2. In addition, after solid selenium recovery conditions were determined, an object of this product of recovering sludge containing highly concentrated Se with an Se content of 30% or more was examined.
(1) Experimental Materials and Method
(1-1) Culture Method for Solid Recovery TSB medium (3000 ml) was introduced into a 5-L volume jar fermenter and subjected to autoclave treatment. Aeration was performed for 1 hour at 38° C., 250 rpm, and 1 L/min. Cells were harvested by centrifuging a preculture solution obtained through preculture of NT-I for 12 hours and were resuspended. A cell suspension was adjusted to $O.D._{660}$=1.0 and then the medium was inoculated with 30 ml (1%) of the cell suspension. Culture was performed under the following culture conditions: 38° C., pH 9.0, 250 rpm, and 1 L/min. After the elapse of 12 hours from the beginning of culture, a 500 mmol/L selenate solution (3 ml) was added to the culture solution for culture.
(1-2) Culture Method for Gas Recovery TSB medium (3000 ml) was introduced into a 5-L volume jar fermenter and subjected to autoclave treatment. Aeration was conducted for 1 hour at 38° C., 250 rpm, and 1 L/min. A 500 mmol/L selenate solution (3 ml) was added to the medium. Cells were harvested by centrifuging a preculture solution obtained through preculture of NT-I for 12 hours and were resuspended. A cell suspension was adjusted to $O.D._{660}$=1.0 and then the medium was inoculated with 30 ml (1%) of the cell suspension. Culture was performed under the following culture conditions: 38° C., pH 9.0, 250 rpm, and 1 L/min.
(1-3) Method for Analyzing Each Phase Measurement samples were prepared and each phase was measured in the manner described in Example 1.

In addition, GC-MS measurement was carried out for qualitative/quantitative determination of a gas phase. Dimethyl selenide (DMSe), dimethyl diselenide (DMDSe), dimethyl sulfide (DMS), and dimethyl disulfide (DMDS) were qualitatively analyzed using authentic preparations in terms of retention time and calibration curves were created for quantitative determination. The structure of dimethyl sulfoselenide (DMSSe) was presumed by GC-MS-MS to determine retention time.
(1-4) Examination of Gaseous Se Trapping by Aeration into Nitrate A Pharmed tube was connected to an exhaust port of a jar fermenter for bubbling into concentrated nitric acid (150 ml) in a 250-ml volume reagent bottle. Air stone was connected to a face of the tube which was in contact with concentrated nitric acid. Concentrated nitric acid was sampled in a time-dependent manner. The selenium concentration was measured by ICP-AES.

In addition, an empty 250-ml volume reagent bottle was connected between the tube and the reagent bottle containing concentrated nitric acid for water vapor trapping.
(1-5) Examination of Gaseous Se Trapping by Activated Carbon In order to examine gaseous Se recovery by activated carbon (SKC: Anasorb CSC, coconut charcoal 226-16), two pieces of activated carbon were connected in series to the exhaust port of the jar fermenter by means of a Pharmed tube. One of the two pieces of activated carbon was connected to the reagent bottle for aeration into nitrate. Palm shell activated carbon was used herein as activated carbon. In addition, an empty 250-ml volume reagent bottle was connected between the other piece of activated carbon and the exhaust port of the jar fermenter for water vapor trapping.

Activated carbon was recovered for 48 hours. Diethyl ether (20 ml) was added thereto for extraction for 30 minutes by an ultrasound device. The extract was subjected to qualitative/quantitative GC-MS analysis and the total Se amount was measured by ICP-AES.
(1-6) Examination of Recovery of Highly Concentrated Solid Se In order to recover sludge containing highly concentrated Se with an Se content of 30% determined as a target level, selenate was added to result in a final concentration of 5 mmol/L, which is 10 times greater than the usual final concentration, followed by culture under solid recovery conditions. A precipitate was recovered from a culture solution by centrifuging the total amount of the culture solution. The obtained precipitate was suspended in 70% ethanol for washing and a suspension was centrifuged to recover a precipitate. After washing was performed again, the precipitate was suspended in 100% ethanol and dried in a draft chamber. The resultant was determined to be Se sludge. Se sludge was dissolved as in the case of dissolution of elemental selenium. The Se concentration was measured by ICP-AES.

(2) Experimental Results and Discussions (2-1) Influence of Aeration on the Decrease in Elemental Selenium FIG. 22 shows the results obtained after culture of the NT-I strain for 12 hours under optimal reduction conditions and the subsequent addition of selenate in a case in which aeration was maintained at 1 L/min and those in a case in which aeration was changed to 0 L/min to stop aeration. It was found that elemental selenium is produced immediately after the addition of selenate in both cases. The rate of elemental selenium production with aeration was greater than that without aeration. The maximum elemental selenium concentration was 0.37 mmol/L in the case in which aeration was maintained. After aeration was stopped, the rate of elemental selenium production relatively decreased; however, the maximum elemental selenium concentration increased to 0.44 mmol/L which was greater than that in the case in which aeration was maintained (FIG. 22A).

The above results show that the decrease in elemental selenium is obviously influenced by aeration and that aeration promotes the decrease in elemental selenium. The rate of the decrease in elemental selenium was calculated. Accordingly, in the case in which aeration was maintained, the rate of the decrease in elemental selenium was $2.6 \times 10^{-18}$ mol/cell/hr, and in the case in which aeration was stopped, the same was $0.5 \times 10^{-18}$ mol/cell/hr. This indicates that aeration promotes the rate of the decrease in elemental selenium to a level approximately 5.3 times greater than that in a case in which aeration is stopped (FIG. 22B).

Based on the above results, optimal reduction conditions were determined to be gaseous selenium recovery conditions. In addition, solid selenium recovery conditions were determined to be 38° C., pH 9.0, 250 rpm, and 0 L/min. Since the termination of aeration significantly influences the growth of bacterial cells, it was decided to recover solid selenium by adding a substrate after cultivating bacterial cells under optimal reduction conditions for 12 hours.

(2-2) Qualitative Analysis of Gaseous Selenium

In order to qualitatively analyze gaseous selenium which was presumed to be generated with the decrease in elemental selenium, a gas phase was measured by GC-MS. FIG. 23 shows typical measurement results. As a result, DMDSe was detected as corresponding to the main peak for jar fermenter culture. In addition, a peak was detected at a retention time corresponding to DMSSe. DMDS was detected as sulfide.

DMSSe was considered to be produced by an equilibrium reaction in the presence of DMDSe and DMDS. Thus, $99.4 \times 10^3$ mg/L DMDSe (350 μl) and $53 \times 10^3$ mg/L DMDS (350 μl) were mixed at room temperature and left to stand in a storage vial bottle in a hermetically-sealed state at an ordinary temperature for 12 hours. Thereafter, a liquid phase was measured by GC-MS. As a result, the DMSSe peak was confirmed at around a retention time of 12.7 min (FIG. 24). This means that DMSSe detected in the gas phase during the culture was probably produced through an equilibrium reaction between DMDSe and DMDS produced through a microorganism reaction.

(2-3) Gas Recovery by Nitrate Trapping and Mass Balance

In order to quantitatively analyze gaseous selenium produced with the decrease in elemental selenium, it was attempted to trap gaseous selenium for gas recovery by introducing an exhaust from a jar fermenter culture into nitrate. Selenate was added under optimal reduction conditions for culture. FIG. 25 shows the results.

As a result, it was found that reduction of selenate/selenite proceeded to produce elemental selenium and then elemental selenium started to decrease, resulting in production of gaseous selenium. After calculation of the yield for each phase at 120 hours after culture, the recovery rate for gaseous selenium at 0.356 mmol/L was 71.2% (table 2). The obtained rate of DMDSe recovery by nitrate trapping was 81.3%. As a result of correction with this value, the corrected recovery rate of gaseous selenium produced was considered to be 87.6%. There is no precedent case in which gaseous selenium produced by a microorganism was quantitatively recovered. The results in this Example were obtained for the first time in the world by achieving recovery of gaseous selenium at a high recovery rate of 70% or more and measurement of the recovery rate over the course of time.

The volatilization rate of a microorganism which has been known as reducing selenate into a negative divalent gaseous selenium is low. It has been reported that *Bacillus* sp. STG-83 volatilizes approximately 0.03% of 1 mmol/L selenate in 4 days when the selenate is added to LB medium, and that *Enterobacter cloacae* SLD1a-1 volatilizes approximately 0.5% of 1 mmol/L selenite in 10 days when the selenite is added to TSB medium. It can be said that the NT-I strain can produce gaseous selenium at a very fast rate during jar fermenter culture compared with these microorganisms.

In addition, since the dissolved selenium concentration did not decrease even after reduction of selenate and selenite, DMDSe or the like was considered to be eluted temporarily in the liquid phase.

The sum of the yields of the respective phases at 120 hours of culture is 85.8% (table 2). In consideration of this value and the rate of recovery of gaseous selenium with the use of nitrateitric acid, a value of 102.2% is obtained. Therefore, it can be said that there is a good mass balance among the gas phase, the liquid phase, and the solid phase for selenate reduction by the NT-I strain.

TABLE 2

Yields for the respective phases under optimal reduction conditions (38° C., pH 9.0, 1 L/min, 250 rpm, 120 h)

| Item | Solution | Solid | Gas | Total | Gas (corrected) | After correction |
|---|---|---|---|---|---|---|
| mmol/L | 0.053 | 0.020 | 0.356 | 0.429 | 0.438 | 0.511 |
| % | 10.5 | 4.0 | 71.2 | 85.8 | 87.6 | 102.2 |

*: The values were calculated based on the efficiency of trapping of methylated selenium with the use of nitrate (81.3%).

(2-4) Examination of Gaseous Selenium Recovery by Activated Carbon

It was attempted to recover gaseous selenium using activated carbon, which can be easily transferred and safely handled, in a method for recovering gaseous selenium. Jar fermenter culture was carried out using the NT-I strain with the addition of selenate under optimal reduction conditions.

Two pieces of activated carbon were connected in series to an exhaust port of a jar fermenter. The piece positioned closed to the jar fermenter was designated as activated carbon (1), and the other piece was designated as activated carbon (2). Aeration was conducted on the back side of activated carbon (2) via nitrate. FIG. 26 shows the element measurement results for activated carbon and nitrate.

As a result, it was found that with respect to the estimated amount of volatilized selenium obtained by subtracting the amounts of elemental selenium and dissolved selenium from the amount of selenate added, 79.9% of gaseous selenium was adsorbed by activated carbon (1) serving as a front part, and 7.6% of gaseous selenium was adsorbed by activated carbon (2) serving as a rear part. It was confirmed by GC-MS that 59.5% of gaseous selenium adsorbed by activated carbon (1) and 14.6% of gaseous selenium adsorbed by activated carbon (2) correspond to DMDSe. The peak of DMSSe was also detected and thus the remaining proportion was considered to correspond to DMSSe. No selenium was detected from the nitrate trap connected to activated carbon. Substantially all gaseous selenium was considered to be adsorbed by activated carbon. The total amount of adsorption by the two pieces of activated carbon is 87.5%. An error of approximately 10% is considered to be influenced by the efficiency of diethyl ether extraction from activated carbon, evaporation of methylated Se during extraction, or the like. There is no precedent case in which microorganism-derived methylated selenium was recovered using activated carbon. The results obtained in this Example demonstrate that a concentrate of methylated selenium was recovered from activated carbon with high efficiency, which was found by the present inventors for the first time in the world.

In addition, desorption due to water vapor might take place after adsorption by activated carbon. Therefore, it would be possible to improve the efficiency of gaseous selenium adsorption by activated carbon by efficiently trapping water vapor in a step prior to the step of adsorption by activated carbon.

(2-5) Recovery of Highly Concentrated Solid Selenium by Control of Aeration

In (2-1) above, the results showing that elemental selenium is allowed to accumulate by controlling aeration were obtained. Therefore, it was attempted to recover solid selenium. Selenate was added to result in a final concentration of 5 mmol/L, which is 10 times greater than the usual final concentration, followed by culture under solid recovery conditions. FIG. 27 shows the results. During culture, the decrease in the selenite concentration stopped and thus aeration was conducted at 1 L/min. Aeration was conducted at a point of time when the decrease in the reduction rate was observed. Aeration was conducted for 10 minutes at 1 L/min and 250 rpm at 33 hours, 1 hour at 1 L/min and 120 rpm at 50 hours, and 8 hours at 1 L/min and 250 rpm at 122 hours.

After culture, all selenite was reduced in 168 hours and 4.39 mmol/L of elemental selenium was produced. At this time, the recovery rate was 87.9%. This was substantially equal to 87.8% obtained when culture was carried out with the addition of 0.5 mmol/L of selenate under the same conditions.

The total amount of the culture solution was recovered at 168 hours of culture at which selenite reduction ended, followed by washing with ethanol and drying. The dried recovered product was designated as Se sludge and the selenium content thereof was measured. As a result, the selenium content per dry weight of the product was found to be 47.1% (w/w) (table 3). The target value in this project was 30% and it was achieved in this Example.

TABLE 3

| Selenium content in Se sludge (% (w/w)) |
| --- |
| ave ± std |
| 47.1 ± 9.2 |

Example 3

Examination of Se Recovery from Actual Wastewater (1) Materials and Experimental Method
(1-1) Analysis of Wastewater Two types of Se-containing wastewater were designated as a solution sample 1 and a solution sample 2. The solution sample 2 was used for experiments. 10-fold (1/10) and 100-fold (1/100) diluted measurement solutions of the solution samples 1 and 2 were prepared and liquid properties thereof were adjusted. Measurement was carried out three times (n=3) by ICP-AES.

(1-2) Culture Method for Solid Recovery

TSB medium (2700 ml) was introduced into a 5-L volume jar fermenter and subjected to autoclave treatment. Aeration was conducted for 1 hour at 38° C., 250 rpm, and 1 L/min. Cells were harvested by centrifuging a preculture solution obtained through preculture of NT-I for 12 hours and were resuspended. A cell suspension was adjusted to $O.D._{660}=1.0$ and then the medium in the jar fermenter was inoculated with 30 ml (1%) of the cell suspension. Culture was carried out under the following culture conditions: 38° C., pH 9.0, 250 rpm, and 1 L/min. At 12 hours after the beginning of culture, the solution sample 2 (300 ml) was added to the culture solution without sterilization.

(1-3) Culture Method for Gas Recovery

TSB medium (2700 ml) was introduced into a 5-L volume jar fermenter and subjected to autoclave treatment. Aeration was conducted for 1 hour at 38° C., 250 rpm, and 1 L/min. The solution sample 2 (300 ml) was added to the medium without sterilization. Cells were harvested by centrifuging a preculture solution obtained through preculture of NT-I for 12 hours and were resuspended. A cell suspension was adjusted to $O.D._{660}=1.0$ and then the medium in the jar fermenter was inoculated with 30 ml (1%) of the cell suspension. Culture was carried out for 120 hours under the following culture conditions: 38° C., pH 9.0, 250 rpm, and 1 L/min.

(1-4) Method for Analyzing Each Phase

Measurement samples were prepared and each phase was measured in the manner described above.

(2) Results and Discussions
(2-1) Analysis of Solution Samples

Table 4 shows the contents of Se in the solution samples. The solution 2 was quantitatively analyzed by ion chromatography. As a result, the solution 2 was found to contain selenate at 4.54 mmol/L and selenite at 0.791 mmol/L. The sum of these values is substantially identical to a measurement result of 5.53 mmol/L obtained by ICP-AES.

Se-containing wastewater is difficult to treat by physicochemical methods because of its high selenate content. The solution samples 1 and 2 were collected at the same site; however, their concentrations were found to be approximately 5 to 10 mmol/L, respectively. Thus, an approximately two-fold difference was obtained. Regarding other elements, the concentrations of almost all elements including Si in the solution sample 1 were greater than those in the solution sample 2.

Since it was found that the NT-I strain maintains its ability to reduce selenate/selenite even at a high concentration of 50 mmol/L, it was considered that it would be possible to apply the NT-I strain to the Se-containing wastewater. Also, among other elements, no element that could inhibit cell growth was detected in the wastewater. Therefore, the wastewater can be regarded appropriate for microorganism treatment.

TABLE 4

Composition of solution samples

| Sample name | Solution sample (1) | | Solution Sample (2) | |
|---|---|---|---|---|
| Element | ave ± std [mmol/L] | CV % | ave ± std [mmol/L] | CV % |
| Se | 10.6 ± 0.2 | (2.1) | 5.53 ± 0.15 | (2.7) |

(2-2) Examination of Solid Se Recovery from Actual Wastewater

FIG. 28 and table 5 show the results of culture under solid recovery conditions. The percentage of solid Se recovered from the wastewater under solid recovery conditions was 78.8%. In the case of a model system, the recovery rate obtained under solid recovery conditions was 87.7%. In this Example, the recovery rate was slightly below that obtained in the model system; however, the obtained recovery rate was still high. Reduction of selenate/selenite proceeded very rapidly to an extent comparable to that in the case of the model system. These results indicate that solid Se can be recovered from the wastewater.

At the recovery point, the yield of liquid Se was 8.6%, and the estimated yield of gaseous Se was 12.5%. This indicates that further advancement in the reaction probably caused advancement in volatilization of solid Se by methylation. Further, it would be necessary to consider handling by, e.g., the control of aeration in order to obtain an improved solid Se recovery rate.

TABLE 5

Yield of each phase upon solid recovery

| Item | Liquid | Solid | Gas (estimated) | Total |
|---|---|---|---|---|
| mmol/L | 0.056 | 0.507 | 0.081 | 0.644 |
| % | 8.6 | 78.8 | 12.5 | 100 |

(38° C., pH 9.0, 1 L/min, 250 rpm, 24 h)

(2-3) Examination of Gaseous Se Recovery from Actual Wastewater

FIG. 29 and table 6 show the results of culture under gas recovery conditions. Gaseous Se was recovered from wastewater under gas recovery conditions at a recovery rate of 38.9% (measured value). In the case of the model system, the recovery rate obtained under gas recovery conditions was 71.2% (measured value). In this Example, the recovery rate was approximately half of that in the case of the model system.

Reduction of selenate/selenite proceeded very rapidly. Reduction of oxyanion took place to an extent comparable to that in the model system. The solid content upon recovery was 3.8%, which decreased to a level substantially equal to 4.0% in the case of the model system. Meanwhile, the content of liquid Se was 35.9% in the wastewater, which was obviously greater than 10.5% in the case of the model system.

The above results indicate that the decrease in the gaseous Se recovery rate was probably due to the presence of Se remaining in liquid upon volatilization of solid Se by methylation. The wastewater was found to contain elements such as K and Ca compared with the model system. These elements might be factors influencing the recovery rate.

TABLE 6

Yield of each phase upon gas recovery

| Item | Liquid | Solid | Gas | Total |
|---|---|---|---|---|
| mmol/L | 0.221 | 0.023 | 0.240 | 0.484 |
| % | 35.9 | 3.8 | 38.9 | 78.6 |

(38° C., pH 9.0, 1 L/min, 250 rpm, 120 h)

TABLE 7

Yield of each phase after correction calculation

| Item | Liquid | Solid | Gas (corrected) | Total |
|---|---|---|---|---|
| mmol/L | 0.221 | 0.023 | 0.295 | 0.539 |
| % | 35.9 | 3.8 | 58.9 | 87.6 |

(38° C., pH 9.0, 1 L/min, 250 rpm, 120 h)
*: The values were calculated based on the efficiency (81.3%) of trapping of methylated selenium with the use of nitrate.

Example 4

Examination of Se Recovery from a Solar Panel

In the Example 4, selenium recovery experiments were conducted in a culture system employing an optimized jar fermenter with the use of a powder sample of a solar panel comprising, as a material, CIGS (i.e., a thin-film substance comprising, as materials, copper (Cu) and a compound of indium (In), gallium (Ga), and selenium (Se)).

(1) Materials and Experimental Method
(1-1) Method for Analyzing the Powder Sample A solution of the sample was prepared using a digestion solution in a microwave sample digestion system. For the digestion solution, concentrated nitric acid (4 ml) and concentrated hydrofluoric acid (4 ml) are used. In addition, in order to dissolve rare earth, boric acid (1 g) was added after digestion to carry out digestion again. Liquid properties of each sample were adjusted, and a stock solution measurement sample and 1000-fold (1/1000) and 100000-fold (1/100000) diluted measurement solutions were prepared. Then, measurement was carried out three times (n=3) using an inductively coupled plasma mass spectrometer (ICP-MS) (X-Series 2, Thermo Fisher Scientific K.K.).

(1-2) Preparation of a Solution Sample 1 and an Analysis Method

A powder sample (1 g) was weighed by an electric balance and introduced into a 50-ml coming tube. Concentrated nitric acid (5 ml) was added to the tube so as to dissolve the sample. Further, 95 ml of ultrapure water was added using a 10-ml pipette to result in a final volume of 100 ml. The resultant was centrifuged for 5 minutes (15,000 rpm) and the thus obtained supernatant was filtered using a disc filter (filter size: 0.2 μm). The solution obtained herein was designated as a solution sample 1. Measurement was carried out using an inductively coupled plasma optical emission spectrometer (ICP-AES) (iCAP 6300 Duo, Thermo Fisher Scientific K.K.). 10-fold (1/10), 100-fold (1/100), and 1000-fold (1/1000) diluted measurement solutions of the sample were prepared and liquid properties thereof were adjusted. Then, measurement was carried out three times by ICP-AES (n=3).

(1-3) Preparation of a Solution Sample 2 and a Neutralized Sample

A powder sample (1 g) was weighed by an electric balance and introduced into a 50-ml corning tube. Concentrated hydrochloric acid (4 ml) and concentrated nitric acid (1 ml) were added to the tube, and the sample was dissolved by microwave for 30 minutes. Further, 95 ml of ultrapure water was added using a 10-ml pipette to result in a final volume of 100 ml. The resultant was centrifuged for 5 minutes (15,000 rpm) and the thus obtained supernatant was filtered using a disc filter (filter size: 0.2 μm). The solution obtained herein was designated as a solution sample 2. The precipitate obtained as a result of centrifugation was designated as an acid dissolution residue and subjected to measurement by ICP-AES. A 5N sodium hydroxide solution (10 ml) was added to the solution sample 2, followed by centrifugation. Thus, the solution was separated into a supernatant and a precipitate. Measurement was carried out by ICP-AES using the obtained supernatant as a neutralized solution sample and the obtained precipitate as a neutralized precipitate. 10-fold (1/10), 100-fold (1/100), and 1000-fold (1/1000) diluted measurement solutions were prepared and liquid properties thereof were adjusted. Then, measurement was carried out three times by ICP-AES (n=3).

(1-4) Culture Method for Solid Recovery

TSB medium (3000 ml) was introduced into a 5-L volume jar fermenter and subjected to autoclave treatment. Aeration was conducted for 1 hour at 38° C., 250 rpm, and 1 L/min. Cells were harvested by centrifuging a preculture solution obtained through preculture of NT-I for 12 hours and were resuspended. A cell suspension was adjusted to $O.D._{660}=1.0$ and then the medium was inoculated with 30 ml (1%) of the cell suspension. Culture was performed under the following culture conditions: 38° C., pH 9.0, 250 rpm, and 1 L/min. After the elapse of 12 hours from the beginning of culture, the solution sample 1 (30 ml) or the neutralized solution sample (40 ml) was added to the culture solution for culture.

(1-5) Culture Method for Gas Recovery

TSB medium (3000 ml) was introduced into a 5-L volume jar fermenter and subjected to autoclave treatment. Aeration was conducted for 1 hour at 38° C., 250 rpm, and 1 L/min. The solution sample 1 (30 ml), the solution sample 2 (30 ml), or the neutralized solution sample (40 ml) was added to the medium without sterilization. Cells were harvested by centrifuging a preculture solution obtained through preculture of NT-I for 12 hours and were resuspended. A cell suspension was adjusted to $O.D._{660}=1.0$ and then the medium was inoculated with 30 ml (1%) of the cell suspension. Culture was carried out under the following culture conditions: 38° C., pH 9.0, 250 rpm, and 1 L/min.

(1-6) Method for Analyzing Each Phase

Measurement samples were prepared and each phase was measured in the manner described above. In addition, nitrate ions and nitrite ions were quantitatively determined by ion chromatography (ICS-1100, Dionex Co., Ltd.). Measurement was carried out by the method described above.

(1-7) Recovery and Measurement of Adherent Matter

Matter adhering to container walls was recovered under gas recovery conditions and subjected to elemental analysis. A collected portion of the sample was dissolved by a method similar to the method for measuring the precipitation sample, followed by ICP-AES analysis.

(2) Results and Discussions (2-1) Results of Analysis of the Powder Sample and the Solution Sample Table 8 shows the Se composition of the powder sample and the Se composition of the solution sample. As a result of quantitative analysis of the solution sample by ion chromatography, no selenate was detected and the concentration of selenite was found to be 45.5 mmol/L. This value was substantially identical to a value of 44.9 mmol/L quantitatively determined by ICP-AES (Table 8).

TABLE 8

Results of multielemental analysis of the powder sample

| Element | ave ± std [mmol · kg$^{-1}$] | CV [%] |
|---|---|---|
| Se | 4520 ± 139 | (4) |
| In | 1570 ± 40 | (3) |
| Cu | 2030 ± 80 | (4) |
| Ga | 570 ± 23 | (4) |
| Zn | 29 ± 1 | (4) |
| Fe | 2 ± 0 | (11) |
| Cr | 2 ± 0 | (8) |

Results of multielemental analysis of the solution sample 1

| Element | ave ± std [mmol · L$^{-1}$] | CV [%] |
|---|---|---|
| Se | 44.9 ± 0.2 | (1) |
| In | 25.4 ± 0.1 | (1) |
| Cu | 28.6 ± 0.2 | (1) |
| Ga | 7.1 ± 0.1 | (1) |

Table 9 shows the composition results for the powder sample that was dissolved in acid to react with a microorganism and the composition results for the neutralized solution sample 2. As a result of neutralization and centrifugation, it was possible to separately obtain Se and Ga in the supernatant and In and Cu in the precipitate.

TABLE 9

Results of multielemental analysis of the solution sample 2

| Element | ave ± std [mmol · L$^{-1}$] | CV [%] |
|---|---|---|
| Se | 43.5 ± 0.3 | (0) |
| In | 26.7 ± 0.0 | (0) |
| Cu | 29.8 ± 1.6 | (0) |
| Ga | 7.6 ± 0.0 | (0) |

Results of multielemental analysis of the neutralization solution

| Element | ave ± std [mmol · L$^{-1}$] | CV [%] |
|---|---|---|
| Se | 38.4 ± 1.2 | (0) |
| In | 0.0 ± 0.0 | (0) |
| Cu | 0.4 ± 0.1 | (0) |
| Ga | 5.8 ± 0.0 | (0) |

(2-2) Examination of Solid Se Recovery from Solution Sample 1

FIG. 30 and table 10 show the results of culture under conditions for solid recovery from the solution sample 1. The recovery rate of solid Se recovered from the solution sample 1 under solid recovery conditions was 27.5%. Since the recovery rate obtained under solid recovery conditions in the model system was 87.7%, it is understood that the recovery rate decreased. In particular, selenite reduction was obviously inhibited. This was probably because of the influence of nitrate used for dissolving the powder sample and the influence of the coexistence of other CIGS elements. FIG. 31 shows behaviors of nitrate/nitrite. It is understood that nitrite produced as a result of nitrate reduction was reduced, and selenite reduction gradually proceeds in parallel with the reduction of nitrite. Therefore, it is considered that the presence of nitrate influences selenite reduction to a certain extent.

TABLE 10

Yield of each phase upon solid recovery

| Item | Liquid | Solid | Gas (estimated) | Total |
|---|---|---|---|---|
| mmol/L | 0.402 | 0.140 | 0 | 0.542 |
| % | 78.9 | 27.5 | 0 | 106.4 |

(38° C., pH 9.0, 1 L/min, 250 rpm, 200 h)

(2-3) Examination of Solid Se Recovery from the Neutralized Solution Sample

In order to reduce the influence of nitrate, the powder sample was dissolved at a decreased concentration of nitrate. Also, in order to reduce the influence of other metal elements, culture was carried out using the neutralized solution sample subjected to neutralization. FIG. 32 and table 11 show the results of culture under conditions for solid recovery from the neutralized sample. The recovery rate of solid Se recovered from the neutralized solution sample was 60.0%. Selenite was very rapidly reduced in the neutralized solution sample. The recovery rate was improved to a level 2.2 times greater than that for the solution sample 1.

During culture, a phenomenon in which the color of the culture solution of the solution sample 1 changed to brownish black. When the neutralized solution sample was used, this phenomenon was not confirmed. It is therefore considered that the recovery rate was improved as a result of removal of Cu and In by neutralization.

In this Example, the maximum elemental selenium concentration was 0.39 mmol/L upon recovery from the neutralized sample, which corresponds to 60.0% of selenium added. Thereafter, the recovery rate of elemental selenium decreased to 23.8% at 120 hours. In the case of the model system, a maximum elemental selenium recovery rate of 87.8% was obtained and the recovery rate decreased to 75.7% at 133 hours. Therefore, it is considered that the decrease was greater than that in the model system, indicating the progression of the production of gaseous selenium. Aeration largely influences the production of gaseous selenium. Thus, it would be possible to prevent the decrease in elemental selenium so as to improve the recovery rate by improving, for example, the control of aeration in culture of 12 hours before the addition of a substrate.

TABLE 11

Yield of each phase upon solid recovery from the neutralized sample

| Item | Liquid | Solid | Gas (estimated) | Total |
|---|---|---|---|---|
| mmol/L | 0.082 | 0.389 | 0.177 | 0.649 |
| % | 12.7 | 60.0 | 27.3 | 100.0 |

(38° C., pH 9.0, 1 L/min, 250 rpm, 27 h)

FIG. 39 shows the summary of rare metal recovery with the use of the solar panel powder sample comprising CIGS (i.e., a thin-film substance, comprising, as materials, copper (Cu) and a compound of indium (In), gallium (Ga), and selenium (Se)) in the culture system employing a jar fermenter in Example 4.

(2-4) Examination of Gaseous Se Recovery from the Solution Sample

FIG. 33 and table 12 show the results of culture under conditions for gas recovery from the solution sample 1. The recovery rate of gaseous Se recovered from the solution sample 1 under gas recovery conditions was 11.9% (measured value). Since the recovery rate obtained under gas recovery conditions in the model system was 71.2% (measured value), it is understood that the recovery rate significantly decreased.

However, in this Example, inhibition of selenite reduction, which was observed in solid recovery conditions, was not observed. Behaviors of nitrate/nitrite shown in FIG. 34 indicate that nitrate is rapidly reduced, while on the other hand, nitrite is not rapidly reduced.

Selenite reduction rapidly proceeded, while the recovery rate of gaseous Se was very low. Unstable values of elemental selenium measurement indicate that produced solid Se was not uniformly dispersed, which probably caused coagulation. It is also probable that solid Se coagulation inhibited the production of gaseous selenium.

TABLE 12

Yield of each phase upon gas recovery from the solution sample 1

| Item | Liquid | Solid | Gas | Total |
|---|---|---|---|---|
| mmol/L | 0.245 | 0.046 | 0.056 | 0.347 |
| % | 52.2 | 9.7 | 11.9 | 73.8 |

Yield of each phase after correction calculation

| Item | Liquid | Solid | Gas (corrected) | Total |
|---|---|---|---|---|
| mmol/L | 0.245 | 0.046 | 0.069 | 0.360 |
| % | 52.2 | 9.7 | 13.7 | 75.6 |

(38° C., pH 9.0, 1 L/min, 250 rpm, 290 h)
*: The values were calculated based on the efficiency (81.3%) of trapping of methylated selenium with the use of nitrate.

(2-5) Examination of Gaseous Se Recovery from the Solution Sample 2

FIG. 35 and table 13 show the results of culture under conditions for gas recovery from the solution sample 2. The recovery rate of gaseous Se recovered from the solution sample 2 under gas recovery conditions was 14.4% (measured value). Since the recovery rate obtained under gas recovery conditions in the model system was 71.2% (measured value), it is understood that although the recovery rate was slightly improved compared with that for the solution sample 1, it was still low.

The results suggest that the coexistence of metal elements such as Cu and In negatively influences gaseous Se recovery to a greater extent compared with the nitrate

TABLE 13

Yield of each phase upon gas recovery from the solution sample 2

| Item | Liquid | Solid | Gas | Total |
|---|---|---|---|---|
| mmol/L | 0.314 | 0.070 | 0.080 | 0.464 |
| % | 56.8 | 12.7 | 14.4 | 83.9 |

TABLE 13-continued

Yield of each phase after correction calculation

| Item | Liquid | Solid | Gas (corrected) | Total |
|---|---|---|---|---|
| mmol/L | 0.314 | 0.070 | 0.098 | 0.482 |
| % | 56.8 | 12.7 | 17.7 | 87.2 |

(38° C., pH 9.0, 1 L/min, 250 rpm, 144 h)
*: The values were calculated based on the efficiency (81.3%) of trapping of methylated selenium with the use of nitrate.

(2-6) Examination of Gaseous Se Recovery from the Neutralized Solution Sample

FIG. 36 and table 14 show the results of culture under conditions for gas recovery from the neutralized solution sample. The recovery rate of gaseous Se recovered from the neutralized solution sample under gas recovery conditions was 44.3% (measured value). The recovery rate obtained in the case of the neutralized solution sample was improved to a level approximately 3.7 times greater than that obtained in the case if the solution sample 1.

This is probably because the coagulation observed in the experiment for recovering gaseous selenium from the solution sample 1 did not occur as a result of the removal of Cu and In through neutralization, facilitating the production of gaseous selenium. Also when elemental selenium was measured, variations in the measurement values of elemental selenium which were probably because of nonuniform dispersion due to coagulation caused by Cu and In were not observed.

The recovery rate was lower than the gaseous Se recovery rate for the model system (71.1%); however, it is considered that the recovery rate would be improved by thoroughly removing metal elements inhibiting the recovery.

TABLE 14

Yield of each phase upon gas recovery from the neutralized sample

| Item | Liquid | Solid | Gas | Total |
|---|---|---|---|---|
| mmol/L | 0.185 | 0.028 | 0.287 | 0.501 |
| % | 28.6 | 4.4 | 44.3 | 77.2 |

Yield of each phase after correction calculation

| Item | Liquid | Solid | Gas (corrected) | Total |
|---|---|---|---|---|
| mmol/L | 0.185 | 0.028 | 0.353 | 0.566 |
| % | 28.6 | 4.4 | 54.4 | 87.4 |

(38° C., pH 9.0, 1 L/min, 250 rpm, 120 h)
*: The values were calculated based on the efficiency (81.3%) of trapping of methylated selenium with the use of nitrate.

Example 5

An experiment for recovering Se from solar panel waste containing Se was conducted using a culture system employing a jar fermenter in Example 5.
(1) Materials and Experimental Method
(1-1) Preparation of a Powder Sample and an Analysis Method A waste powder sample (0.25 g) containing Se was collected and dissolved in concentrated nitric acid (10 ml) used as a digestion solution. A sample solution was obtained using the digestion solution by a microwave sample digestion system. Liquid properties of each sample were adjusted, and a stock solution measurement sample and 1000-fold (1/1000) and 100000-fold (1/100000) diluted measurement solutions were prepared. Then, measurement was carried out three times using an inductively coupled plasma mass spectrometer (ICP-MS) (iCAP 6300 Duo, Thermo Fisher Scientific K.K.). The measurement number is n=3.

(1-2) Preparation of a Solution Sample and an Analysis Method

A powder sample (2 g) was weighed by an electric balance and introduced into a 50-ml coming tube. Concentrated nitric acid (10 ml) was dispensed into the tube (1 ml per injection) using a 1000-ul variable micropipette so as to dissolve the sample. Further, 20 ml of ultrapure water was added using a 10-ml pipette to result in a final volume of 30 ml. The resultant was centrifuged for 5 minutes (15,000 rpm) and the thus obtained supernatant was filtered using a disc filter (filter size: 0.2 μm). The solution obtained herein was designated as an acid dissolution sample. The precipitate obtained as a result of centrifugation was designated as an acid dissolution residue. Measurement was carried out using an inductively coupled plasma optical emission spectrometer (ICP-AES) (iCAP 6300 Duo, Thermo Fisher Scientific K.K.). A 5N sodium hydroxide solution (30 ml) was added to the obtained acid dissolution sample. The resultant was centrifuged for 5 minutes (15,000 rpm) in order to remove the produced precipitate. Thus, the supernatant solution and the precipitate were separated. The precipitate obtained herein was designated as a neutralized precipitate. The supernatant solution obtained herein was filtered using a disc filter (filter size: 0.2 μm).

The above steps were repeated three times to mix the solutions so as to prepare a solution sample (total volume: 150 ml). 10-fold (1/10), 100-fold (1/100), and 1000-fold (1/1000) diluted measurement solutions of each sample were prepared and liquid properties thereof were adjusted. Then, measurement of the solution sample was carried out three times by ICP-AES. The measurement number is n=3.

(1-3) Culture Method for Solid Recovery

TSB medium (3000 ml) was introduced into a 5-L volume jar fermenter and subjected to autoclave treatment. Aeration was conducted for 1 hour at 38° C., 250 rpm, and 1 L/min. Cells were harvested by centrifuging a preculture solution obtained through preculture of NT-I for 12 hours and were resuspended. A cell suspension was adjusted to O.D.$_{660}$=1.0 and then the medium was inoculated with 30 ml (1%) of the cell suspension. Culture was performed under the following culture conditions: 38° C., pH 9.0, 250 rpm, and 1 L/min. After the elapse of 12 hours from the beginning of culture, a solution sample (50 ml) was added to the culture solution for culture.

(1-4) Culture Method for Gas Recovery

TSB medium (3000 ml) was introduced into a 5-L volume jar fermenter and subjected to autoclave treatment. Aeration was conducted for 1 hour at 38° C., 250 rpm, and 1 L/min. The solution sample (50 ml) was added to the medium without sterilization. Cells were harvested by centrifuging a preculture solution obtained through preculture of NT-I for 12 hours and were resuspended. A cell suspension was adjusted to O.D.$_{660}$=1.0 and then the medium was inoculated with 30 ml (1%) of the cell suspension. Culture was performed under the following culture conditions: 38° C., pH 9.0, 250 rpm, and 1 L/min.

(1-5) Method for Analyzing Each Phase

Measurement samples were prepared and each phase was measured in the manner described above.

(2) Results and Discussions
(2-1) Powder Sample Analysis Results, Solution Sample Preparation, and Changes in the Element Concentrations Over the Course of Solution Sample Preparation As a result of measurement of the powder sample, Se, which is a major component of waste containing selenium, was detected. The Se concentration was 908 mmol/kg.

The Se concentration in the solution sample was 30.6 mmol/L. As a result of quantitative analysis by ion chromatography, no selenate was detected and the concentration of selenite was found to be 28.6 mmol/L.

(2-2) Examination of Recovery of Solid Se from the Solution Sample

FIG. 37 and table 15 show the results of culture under solid recovery conditions. The recovery rate of solid Se recovered from the waste-dissolved solution under solid recovery conditions was 83.6%. Since the recovery rate obtained under solid recovery conditions in the model system was 87.7%, the obtained recovery rate was high and comparable to that for the model system. Reduction of selenate/selenite also proceeded very rapidly. This means that it is possible to recover solid Se from the waste containing Se.

TABLE 15

Yield of each phase upon solid recovery

| Item | Liquid | Solid | Gas (estimated) | Total |
|---|---|---|---|---|
| mmol/L | 0.046 | 0.483 | 0.049 | 0.578 |
| % | 7.9 | 83.6 | 8.4 | 100.0 |

(38° C., pH 9.0, 1 L/min, 250 rpm, 12 h)

(2-3) Examination of Gaseous Se Recovery from the Solution Sample

FIG. 38 and table 16 show the results of culture under gas recovery conditions. The recovery rate of gaseous selenium was 21.1% (measured value). Since the recovery rate obtained under gas recovery conditions in the model system was 71.2% (measured value), the obtained recovery rate was found to correspond to approximately one-third of that for the model system.

Reduction of selenate/selenite proceeded very rapidly. Oxyanion reduction in this Example was comparable to that in the model system. Also, solid Se was found to have rapidly decreased. The recovery rate of solid Se upon gas recovery (48 h) was 12.7%; however, it decreased to 4.0% at 144 hours. This can be comparable to a level of 4.0% for the model system. Meanwhile, the content of liquid Se was very high. The recovery rate of liquid Se was 49.5% upon gas recovery (48 h) and 53.9% even at 144 hours. It is very higher than a level of 10.5% for the model system.

Based on the above results, it is considered that the decrease in the recovery rate of gaseous Se was due to the presence of remaining unidentified Se in liquid upon evaporation of solid Se by methylation. This is probably because of the influence of a waste-derived element remaining in the solution sample.

TABLE 16

Yield of each phase upon gas recovery

| Item | Liquid | Solid | Gas | Total |
|---|---|---|---|---|
| mmol/L | 0.260 | 0.067 | 0.111 | 0.438 |
| % | 49.5 | 12.7 | 21.1 | 83.3 |

TABLE 16-continued

Yield of each phase after correction calculation

| Item | Liquid | Solid | Gas (corrected) | Total |
|---|---|---|---|---|
| mmol/L | 0.260 | 0.067 | 0.136 | 0.463 |
| % | 49.5 | 12.7 | 27.3 | 89.6 |

(38° C., pH 9.0, 1 L/min, 250 rpm, 48 h)
*: The values were calculated based on the efficiency (81.3%) of trapping of methylated selenium with the use of nitrate.

Example 6

FIG. 40 shows a photograph of elemental selenium produced in the above Example.

Example 7

Estimates of the Amounts of Rare Metals Recovered from CIGS Solar Cell Powder

FIG. 41 shows the estimates of the amounts of rare metals recovered from CIGS solar cell powder.

The invention claimed is:

1. A method for recovering selenium, comprising:
obtaining a sample containing a water-soluble selenium compound by dissolving a material containing copper (Cu), indium (In), gallium (Ga), and selenium (Se) in an inorganic acid and adding an alkaline aqueous solution for neutralization to remove copper (Cu) and indium (In);
reducing the water-soluble selenium compound so as to produce gaseous selenium by allowing the sample containing the water-soluble selenium compound to come into contact at a temperature of 35° C. to 40° C. and at pH 7.0 to 9.4 with *Pseudomonas stutzeri* NT-I (Accession No. NITE BP-685) serving as a microorganism capable of producing elemental selenium through reduction of a water-soluble selenium compound, under aeration conditions of 1 L/minute to 5 L/minute and under stirring conditions of a stirring rate of 250 rpm or less; and trapping the generated gaseous selenium by aeration into nitrate to recover the gaseous selenium.

2. The method according to claim 1, wherein the water-soluble selenium compound is selenate or selenite.

3. The method according to claim 1, wherein the sample containing a water-soluble selenium compound has a selenium concentration of 100 to 6000 μmol/L.

4. The method according to claim 1, wherein the selenium-containing material is a panel material.

5. The method according to claim 1, wherein the selenium-containing material is a solar cell panel.

6. A method for recovering selenium, comprising:
obtaining a sample containing a water-soluble selenium compound by dissolving a material containing copper (Cu), indium (In), gallium (Ga), and selenium (Se) in inorganic acid and adding an alkaline aqueous solution for neutralization to remove copper (Cu) and indium (In);
culturing *Pseudomonas stutzeri* NT-I (Accession No. NITE BP-685) serving as a microorganism capable of producing elemental selenium through reduction of a water-soluble selenium compound at a temperature of 35° C. to 40° C. and at pH 7.0 to 9.4 under aeration conditions of 1 L/minute to 5 L/minute and under stirring conditions of a stirring rate of 250 rpm or less;
adding the sample containing the water-soluble selenium compound therein;
stopping aeration;
performing the culturing without the aeration conditions; and
recovering the generated elemental selenium.

7. The method according to claim 6, wherein the water-soluble selenium compound is selenate or selenite.

8. The method according to claim 6, wherein the sample containing a water-soluble selenium compound has a selenium concentration of 100 to 6000 μmol/L.

9. The method according to claim 6, wherein the selenium-containing material is a panel material.

10. The method according to claim 6, wherein the selenium-containing material is a solar cell panel.

11. The method according to claim 6, wherein *Pseudomonas stutzeri* NT-I (Accession No. NITE BP-685) is cultured at a temperature of 37° C. to 39° C. and at pH 8.0 to 9.0.

12. The method according to claim 6, wherein *Pseudomonas stutzeri* NT-I (Accession No. NITE BP-685) is cultured at a temperature of approximately 38° C. and at pH approximately 9.0.

13. The method according to claim 1, wherein *Pseudomonas stutzeri* NT-I (Accession No. NITE BP-685) is cultured at a temperature of 37° C. to 39° C. and at pH 8.0 to 9.0.

14. The method according to claim 1, wherein *Pseudomonas stutzeri* NT-I (Accession No. NITE BP-685) is cultured at a temperature of approximately 38° C. and at pH approximately 9.0.

* * * * *